(12) United States Patent
George et al.

(10) Patent No.: US 8,598,199 B2
(45) Date of Patent: *Dec. 3, 2013

(54) OCTAHYDROPENTALENE COMPOUNDS AS CHEMOKINE RECEPTOR ANTAGONISTS

(75) Inventors: Dawn M. George, Charlton, MA (US); Lu X. Wang, Northborough, MA (US); Biqin Li, Southborough, MA (US); Anna M. Ericsson, Shrewsbury, MA (US); Graham K. Ansell, Millbury, MA (US)

(73) Assignee: AbbVie Inc., North Chicago, IL (US)

( * ) Notice: Subject to any disclaimer, the term of this patent is extended or adjusted under 35 U.S.C. 154(b) by 117 days.

This patent is subject to a terminal disclaimer.

(21) Appl. No.: 13/074,676

(22) Filed: Mar. 29, 2011

(65) Prior Publication Data
US 2011/0178096 A1 Jul. 21, 2011

Related U.S. Application Data

(62) Division of application No. 12/284,758, filed on Sep. 25, 2008, now Pat. No. 7,939,544.

(60) Provisional application No. 60/995,148, filed on Sep. 25, 2007.

(51) Int. Cl.
*A01N 43/42* (2006.01)
*A61K 31/44* (2006.01)
*C07D 221/02* (2006.01)

(52) U.S. Cl.
USPC ............................................ 514/299; 546/112

(58) Field of Classification Search
USPC .......................................... 514/299; 546/112
See application file for complete search history.

(56) References Cited

U.S. PATENT DOCUMENTS

| 6,090,382 | A | 7/2000 | Salfeld et al. |
|---|---|---|---|
| 2005/0192302 | A1 | 9/2005 | Xue et al. |
| 2005/0267146 | A1 | 12/2005 | Xue et al. |
| 2007/0032526 | A1 | 2/2007 | Carter et al. |

FOREIGN PATENT DOCUMENTS

| WO | WO8910961 A1 | 11/1989 |
|---|---|---|
| WO | WO 02/44181 | * 6/2002 |
| WO | WO0244181 A1 | 6/2002 |
| WO | WO2005037779 A | 4/2005 |
| WO | WO200504426 A1 | 5/2005 |

OTHER PUBLICATIONS

Banker, Gilbert S. et al., "Modern Pharmaceutics, Marcel Dekker", 1996.
Bazan J.F., et al., "A New Class of Membrane-bound Chemokine With a CX3C Motif," Nature, 1997, vol. 385, pp. 640-644.
Ben-Baruch A., et al., "Monocyte Chemotactic Protein-3 (Mcp3) Interacts With Multiple Leukocyte Receptors. C-C Ckr1, A Receptor For Macrophage Inflammatory Protein-1 α/Rantes, is also a Functional Receptor for MCP3," Journal of Biological Chemistry, 1995, vol. 270 (38), pp. 22123-22128.
Campbell J.J., et al., "6-C-kine (SLC), a Lymphocyte Adhesion-triggering Chemokine Expressed by High Endothelium, is an Agonist for the MIP-3β Receptor CCR7," Journal of Cell Biology, 1998, vol. 141 (4), pp. 1053-1059.
Chaudhuri A., et al., "Expression of the Duffy Antigen in K562 Cells," Journal of Biological Chemistry, 1994, vol. 269 (11), pp. 7835-7838.
Dairaghi D.J., et al., "HHV8-encoded vMIP-I Selectively Engages Chemokine Receptor CCR8," Journal of Biological Chemistry, 1999, vol. 274 (31), pp. 21569-21574.
Deng H., et al., "Identification of a Major Co-receptor for Primary Isolates of HIV-1," Nature, 1996, vol. 381, pp. 661-666.
Fingl E., et al., Pharmacokinetics, Chapter 1, 1975, pp. 1-46.
Greaves D.R., et al., "CCR6, a CC Chemokine Receptor that Interacts with Macrophage Inflammatory Protein 3α and is Highly Expressed in Human Dendritic Cells," Journal of Experimental Medicine, 1997, vol. 186 (6), pp. 837-844.
Horuk R., "Molecular Properties of the Chemokine Receptor Family," Trends in Pharmacological Sciences, 1994, vol. 15 (5), pp. 159-165.
Imai T., et al., "Macrophage-derived Chemokine is a Functional Ligand for the CC Chemokine Receptor 4," Journal of Biological Chemistry, 1998, vol. 273 (3), pp. 1764-1768.
Kelner G.S., et al., "Lymphotactin: A Cytokine that Represents a New Class of Chemokine," Science, 1994, vol. 266 (5189), pp. 1395-1399.
Murphy P.M., et al., "The Molecular Biology of Leukocyte Chemoattractant Receptors," Annual Review of Immunology, 1994, vol. 12, pp. 593-633.
Neote K., et al., "Molecular Cloning, Functional Expression, and Signaling Characteristics of a C-C Chemokine Receptor," Cell, 1993, vol. 72 (3), pp. 415-425.

(Continued)

*Primary Examiner* — Erich A Leeser

(57) ABSTRACT

The present invention is directed to novel compounds of Formula (I)

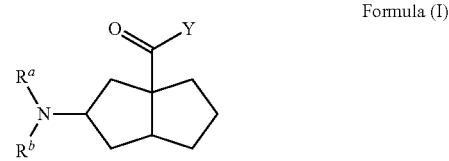

Formula (I)

pharmaceutically acceptable salts thereof, pro-drugs thereof, biologically active metabolites thereof, isomers thereof or stereoisomers thereof wherein the variables are as defined herein. The compounds of Formula (I) are useful as chemokine receptor antagonists and as such would be useful in treating certain conditions and diseases, especially inflammatory conditions and diseases and proliferative disorders and conditions, for example, rheumatoid arthritis, osteoarthritis, multiple sclerosis and asthma.

20 Claims, No Drawings

(56) References Cited

OTHER PUBLICATIONS

Nibbs R.J., et al., "Cloning and Characterization of a Novel Promiscuous Human β Chemokine Receptor D6," Journal of Biological Chemistry, 1997, vol. 272 (51), pp. 32078-32083.

O'Malley R.F., et al., "Anodic Fluorination of Benz[a]anthracene," Journal of Organic Chemistry, 1981, vol. 46 (13), pp. 2816-2818.

Ponath P.D., et al., "Molecular Cloning and Characterization of a Human Eotaxin Receptor Expressed Selectively on Eosinophils," Journal of Experimental Medicine, 1996, vol. 183 (6), pp. 2437-2448.

Remington J.P., "Pharmaceutical Sciences", MACK Publishing Company, 1990, Table of Contents.

Samson M., et al., "Molecular Cloning and Functional Expression of a New Human CC-Chemokine Receptor Gene," Biochemistry, 1996, vol. 35 (11), pp. 3362-3367.

Schall T.J., "Biology of the Rantes/Sis Cytokine Family," Cytokine, 1991, vol. 3 (3), pp. 165-183.

Schall T.J., et al., "Hemokines, Leukocyte Trafficking, and Inflammation," Current Opinion in Immunology, 1994, vol. 6, pp. 865-873.

Wolff, Mandred E., "Burger's Medicinal Chemistry and Drug Discovery," Principles and Practice, 1995, 975-977, 5th Ed,vol. 1, John Wiley & Sons.

Zaballos A., et al., "Cutting Edge: Identification of the Orphan Chemokine Receptor GPR-9-6 as CCR9, the Receptor for the Chemokine TECK," Journal of Immunology, 1999, vol. 162 (10), pp. 5671-5675.

International Search Report dated Dec. 5, 2008; Written Opinion dated Dec. 5, 2008; and International Preliminary Report on Patentability dated Aug. 3, 2010, for PCT/US08/11146.

* cited by examiner

OCTAHYDROPENTALENE COMPOUNDS AS CHEMOKINE RECEPTOR ANTAGONISTS

CROSS REFERENCE TO RELATED APPLICATION

This application is a divisional of U.S. application Ser. No. 12/284,758 filed on Sep. 25, 2008, which claims priority to U.S. Provisional Application Ser. No. 60/995,148 filed on Sep. 25, 2007, the contents of which are incorporated herein.

BACKGROUND OF THE INVENTION

Chemokines are chemotactic cytokines that are released by a wide variety of cells to attract leukocytes, as illustrated by macrophages, T cells, B cells, eosinophils, basophils, and neutrophils to and from sites of inflammation or within specific compartments, as illustrated by lymph nodes (reviewed in Schall, *Cytokine*, 3:165-183 (1991), Schall, et al., *Curr. Opin. Immunol.*, 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ($[Ca^{2+}]$), granule exocytosis, integrin upregulation, formation of bioactive lipids (e.g., leukotrienes), and respiratory burst, associated with leukocyte activation. Thus, the chemokines are early modulators of inflammatory response, effecting inflammatory mediator release, chemotaxis and extravasation to sites of infection or inflammation.

There are four classes of chemokines, CXC ($\alpha$), CC ($\beta$), C ($\gamma$), and $CX_3C$ ($\delta$), depending on whether the first two cysteines are separated by a single amino acid (C-X-C), are adjacent (C-C), have a missing cysteine pair (C), or are separated by three amino acids ($CX_3C$). The $\alpha$-chemokines, such as interleukin-8 (IL-8), melanoma growth stimulatory activity protein (MGSA), and stromal cell derived factor 1 (SDF-1) are chemotactic primarily for neutrophils and lymphocytes, whereas $\beta$-chemokines, such as RANTES, MIP-1$\alpha$, MIP-1$\beta$, monocyte chemotactic protein-1 (MCP-1), MCP-2, MCP-3, and eotaxin are chemotactic for macrophages, T-cells, eosinophils and basophils (Deng, et al., *Nature*, 381: 661-666 (1996)). The C chemokine lymphotactin shows specificity for lymphocytes (Kelner, et al., *Science*, 266: 1395-1399 (1994)) while the $CX_3C$ chemokine fractalkine shows specificity for lymphocytes and monocytes (Bazan, et al., *Nature*, 385:640-644 (1997)).

Chemokines bind specific cell-surface receptors belonging to the family of G-protein-coupled seven-transmembrane-domain proteins (reviewed in Horuk, *Trends Pharm. Sci.*, 15:159-165 (1994)) termed "chemokine receptors." On binding their cognate ligands, chemokine receptors transduce an intracellular signal through the associated heterotrimeric G protein, resulting in a rapid increase in intracellular calcium concentration. There are at least twelve human chemokine receptors that bind or respond to $\beta$-chemokines with the following characteristic pattern: CCR1 (or "CKR-1" or "CC-CKR-1") MIP-1$\alpha$, MIP-1$\beta$, MCP-3, RANTES (Ben-Barruch, et al., *J. Biol. Chem.*, 270:22123-22128 (1995); Neote, et al., *Cell*, 72:415425 (1993)); CCR2A and CCR2B (or "CKR-2A"/"CKR-2A" or "CC-CKR-2A"/"CC-CKR2A") MCP-1, MCP-2, MCP-3, MCP-4; CCR3 (or "CKR-3" or "CC-CKR-3") eotaxin, RANTES, MCP; (Ponath, et al., *J. Exp. Med.*, 183:2437-2448 (1996)); CCR4 (or "CKR-4" or "CC-CKR-4") TARC, MDC (Imai, et al., *J. Biol. Chem.*, 273:1764-1768 (1998)); CCR5 (or "CKR-5" or "CC-CKR-5") MIP-1$\alpha$, RANTES, MIP-1$\beta$; (Sanson, et al., *Biochemistry*, 35:3362-3367 (1996)); CCR6MIP-3a (Greaves, et al., *J. Exp. Med.*, 186:837-844 (1997)); CCR7MIP-3$\beta$ and 6Ckine (Campbell, et al., *J. Cell. Biol.*, 141:1053-1059 (1998)); CCR8 I-309, HHV8 vMIP-I, HHV-8 vMIP-II, MCV vMCC-I (Dairaghi, et al., *J. Biol. Chem.*, 274:21569-21574 (1999)); CCR9 TECK (Zaballos, et al., *J. Immunol.*, 162:5671-5675 (1999)), D6 MIP-1 beta, RANTES, and MCP-3 (Nibbs, et al., *J. Biol. Chem.*, 272:32078-32083 (1997)), and the Duffy blood-group antigen RANTES, MCP-1 (Chaudhun, et al., *J. Biol. Chem.*, 269:7835-7838 (1994)).

Chemokine receptors, such as CCR1, CCR2, CCR3, CCR4, CCR5, CCR6, CCR7, CCR8, CCR9, CXCR1, CXCR2, CXCR3, CXCR4, CXCR5, $CX_3CR1$, and XCR1 have been implicated as being important mediators of inflammatory and immunoregulatory disorders and diseases, including asthma and allergic diseases, as well as autoimmune pathologies such as rheumatoid arthritis and atherosclerosis.

The CCR2 chemokine receptor is expressed primarily in monocytes and activated T lymphocytes, and its functional activity can be measured by cytosolic calcium elevation or chemotaxis. CCR2 exists in two isoforms, CCR2A and CCR2B. These two isoforms are alternatively spliced variants of a single MCP-1 receptor gene and differ only in the carboxyl-terminal tails. The chromosomal location of the CCR2 gene is localized to 3p21. Ligands that have been identified that are selective and of high affinity are the CC chemokines, MCP-1, MCP-2, MCP-3 and MCP-4.

The highly selective expression of CCR2 makes it an ideal target for intervention to interrupt inappropriate monocyte and T cell trafficking. The clinical indications for such intervention are in inflammatory diseases and T-cell mediated autoimmune diseases such as multiple sclerosis, rheumatoid arthritis, asthma, allergy, chronic obstructive pulmonary disease, atherosclerosis, restinosis, type I and type II diabetes, metabolic syndrome and neuropathic pain. Ectopic expression of MCP-1 and CCR2 in certain tumors indicate that selective antagonists of CCR2 will have value in tumor immunotherapy, particularly attenuation of metastasis.

In view of the clinical importance of CCR2, the identification of compounds that modulate CCR2 function represents an attractive avenue into the development of new therapeutic agents. Such compounds are provided herein.

SUMMARY OF INVENTION

In a first embodiment the invention provides a compound of Formula (I)

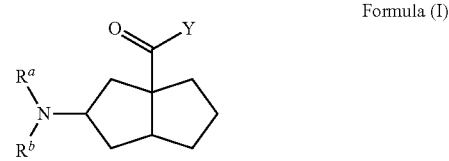

Formula (I)

pharmaceutically acceptable salts thereof, pro-drugs thereof, biologically active metabolites thereof or isomers thereof wherein $R^a$ is H or optionally substituted ($C_1$-$C_6$)alkyl;

$R^b$ is selected from the optionally substituted group consisting of —$(CH_2)_n$-aryl, —$CH(CH_3)$-aryl, —$(CH_2)_n$-aryl-aryl, —$(CH_2)_n$-aryl-heteroaryl, —$(CH_2)_n$—($C_3$-$C_8$)cycloalkyl, —$(CH_2)_n$-heteroaryl, —$(CH_2)_n$-heterocyclyl and —($C_3$-$C_8$)cycloalkyl-aryl; or R$^a$ and R$^b$ are taken together with the nitrogen to form 2,3-dihydro-1H-isoindolyl, decahydroisoquinolinyl, optionally substituted piperidinyl or optionally substituted pyrrolidinyl;

Y is selected from the optionally substituted group consisting of 5,6,7,8-tetrahydro[1,6]naphthridinyl, —NH—(CH$_2$)$_n$-heterocyclyl wherein the NH is attached to the carbonyl and -heterocyclyl-aryl wherein the heterocyclyl is attached to the carbonyl; and n is 0, 1 or 2.

In a second embodiment the invention provides a compound according to the foregoing embodiment wherein Y is selected from the optionally substituted group consisting of 5,6,7,8-tetrahydro[1,6]naphthridinyl, —NH—(CH$_2$)$_2$-pyrrolidinyl and -piperazinyl-phenyl.

In a third embodiment the invention provides a compound according to any of the foregoing embodiments wherein R$^a$ is H or methyl.

In a fourth embodiment the invention provides a compound according to any of the foregoing embodiments wherein R$^b$ is selected from the optionally substituted group consisting of —CH$_2$-phenyl, —CH$_2$-phenyl-phenyl, —(CH$_2$)$_2$-phenyl, —CH(CH$_3$)-phenyl, —CH$_2$CH$_2$-phenyl-phenyl, —CH$_2$-phenyl-pyrazolyl, phenyl-pyrazolyl, indanyl, —(CH$_2$)$_2$-indolyl, 1,2,3,4-tetrahydronaphthyl, —(CH$_2$)-pyrazinyl, —(CH$_2$)$_2$-pyrazinyl, —(CH$_2$)-pyridinyl, —(CH$_2$)$_2$-pyridinyl, —(CH$_2$)$_2$-pyrrolidinyl, —(CH$_2$)$_2$-thienyl, tetrahydrothienyl-1,1-dioxide, —(CH$_2$)$_2$-piperidinyl, tetrahydropyranyl and -cyclohexyl-phenyl.

In a fifth embodiment the invention provides a compound according to any of the foregoing embodiments wherein R$^b$ is selected from the optionally substituted group consisting of —CH$_2$-phenyl, —(CH$_2$)$_2$-phenyl, —CH$_2$-phenyl-pyrazolyl, indanyl, —(CH$_2$)$_2$-indolyl, 1,2,3,4-tetrahydronaphthyl, —(CH$_2$)$_2$-pyridinyl and -cyclohexyl-phenyl.

In a sixth embodiment the invention provides a compound according to any of the foregoing embodiments wherein Y is selected from the optionally substituted group consisting of 5,6,7,8-tetrahydro[1,6]naphthyridinyl and -piperazinyl-phenyl.

In a seventh embodiment the invention provides a compound according to any of the foregoing embodiments wherein R$^b$ is selected from the optionally substituted group consisting of —CH$_2$-phenyl, —(CH$_2$)$_2$-phenyl, 1,2,3,4-tetrahydronaphthyl, —CH$_2$-phenyl-pyrazolyl, indanyl, —(CH$_2$)$_2$-pyridinyl and -cyclohexyl-phenyl.

In an eighth embodiment the invention provides a compound according to any of the foregoing embodiments wherein R$^b$ is selected from the optionally substituted group consisting of —CH$_2$-phenyl, 1,2,3,4-tetrahydronapthyl and -cyclohexyl-phenyl.

In a ninth embodiment the invention provides a compound according to any of the foregoing embodiments wherein R$^b$ is optionally substituted with one or more substituents selected from the group consisting of alkyl, alkoxy, halogen, CN, OH, CF$_3$, OCF$_3$, NH$_2$, NH(CH$_3$) and N(CH$_3$)$_2$.

In a tenth embodiment the invention provides a compound according to any of the foregoing embodiments wherein Y is optionally substituted with CF$_3$.

In an eleventh embodiment the invention provides a compound according to any of the foregoing embodiments wherein R$^a$ and R$^b$ are taken together with the nitrogen to form 2,3-dihydro-1H-isoindolyl, 5,6,7,8-tetrahydro[1,6]naphthyridinyl, optionally substituted piperidinyl or optionally substituted pyrrolidinyl.

In a twelfth embodiment the invention provides a compound according to the eleventh embodiment wherein the optionally substituted piperidinyl or optionally substituted pyrrolidinyl is optionally substituted by substituents selected from the group consisting of optionally substituted cyclohexyl and optionally substituted phenyl.

In a thirteenth embodiment the invention provides a compound according to any of the foregoing embodiments wherein Y is optionally substituted 5,6,7,8 tetrahydro[1,6] naphthyridinyl.

In a fourteenth embodiment the invention provides a compound according to the thirteenth embodiment wherein the optionally substituted piperidinyl is substituted with optionally substituted phenyl or optionally substituted pyrrolidinyl.

In a fifteenth embodiment the invention provides a compound according to fourteenth embodiments wherein the optionally substituted piperidinyl is substituted with optionally substituted pyrrolidinyl.

In a sixteenth embodiment the invention provides a compound according to the fourteenth embodiment wherein the optionally substituted piperidinyl is substituted with optionally substituted phenyl.

In a seventeenth embodiment the invention provides a compound according to twelfth embodiment wherein the optionally substituted pyrrolidinyl is substituted by optionally substituted cyclohexyl.

In an eighteenth embodiment the invention provides a method of treating a condition in a patient comprising administering a therapeutically effective amount of a compound of claim 1 or a physiologically acceptable salt thereof to said patient, wherein said condition is selected from the group consisting of rheumatoid arthritis, osteoarthritis, asthma, chronic obstructive pulmonary disease, sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy, systemic lupus erythematosus, an ocular condition, a cancer, a solid tumor, fibrosarcoma, osteoma, melanoma, retinoblastoma, a rhabdomyosarcoma, glioblastoma, neuroblastoma, teratocarcinoma, an cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, alpha-1 antitrypsin deficiency, amyotrophic lateral sclerosis, anemia, angina pectoris, anterior horn cell degeneration, anti cd3 therapy, antiphospholipid syndrome, anti-receptor hypersensitivity reactions, hypersensitivity reactions, hyperkinetic movement disorders, hypersensitivity pneumonitis, hypertension, hypokinetic movement disorders, aortic and peripheral aneurysms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, Subacute sclerosing panencephalitis, Syncope, syphilis of the cardiovascular system, systemic anaphylaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, atrial fibrillation (sustained or paroxysmal), atrial flutter, atrioventricular block, B cell lymphoma, bone graft rejection, bone marrow transplant (BMT) rejection, small bowel transplant rejection, spinal ataxia, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia, chronic alcoholism, chronic inflammatory pathologies, chronic lymphocytic leukemia, chronic salicylate intoxication, colorectal carcinoma, congestive heart failure, conjunctivitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetic ateriosclerotic disease, Diffuses Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, gram negative sepsis, gram positive sepsis, granulomas due to intracellular organisms, hairy cell leukemia, Hallerrorden-Spatz disease, hay fever, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile rheumatoid arthritis, juvenile spinal muscular atrophy, kidney transplant rejection, legionella, leishmaniasis, lipedema, liver transplant rejection, lymphederma, malaria, malignant Lymphoma, malignant histiocytosis, malignant melanoma, meningococcemia, metabolic/idiopathic, migraine headache, mitochondrial multi-system disorder, monoclonal gammopathy, multiple myeloma, multiple systems degenerations (Mencel Dejerine-Thomas Shi-Drager and Machado-Joseph), *myasthenia gravis, mycobacterium avium* intracellulare, mycobacterium tuberculosis, myelodyplastic syndrome, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, Kaposi's sarcoma, Hodgkin's disease, lymphoma, myeloma, leukaemia, malignant ascites, hematopoietic cancers, Crow-Fukase (POEMS) syndrome (polyneuropathy, organomegaly, endocrinopathy, monoclonal gammopathy, and skin changes syndrome), a diabetic condition such as insulin-dependent diabetes mellitus glaucoma, diabetic retinopathy or microangiopathy, sickle cell anaemia, chronic inflammation, synovitis, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, Progressive supranucleo Palsy, primary pulmonary hypertension, radiation therapy, Raynaud's phenomenon and disease, Refsum's disease, regular narrow QRS tachycardia, renovascular hypertension, restrictive cardiomyopathy, sarcoma, senile chorea, Senile Dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, postlaser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, H is bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci infection, mental disorders (e.g., depression and schizophrenia), Th2 Type and Th1 Type mediated diseases, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome, proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, age-related macular degeneration, acute idiopathic polyneuritis, acuter or chronic immune disease associated with organ transplantation, acute inflammatory demyelinating polyradiculoneuropathy, acute ischemia, adult Still's disease, allergy, anaphylaxis, anti-phospholipid antibody syndrome, aplastic anemia, atopic eczema, atopic dermatitis, autoimmune dermatitis, autoimmune diabetes, autoimmune disorder associated with streptococcus infection, autoimmune enteropathy, autoimmune hepatitis, autoimmune hearing loss, autoimmune lymphoproliferative syndrome, autoimmune myocarditis, autoimmune neutropenia, autoimmune premature ovarian failure, autoimmune thrombocytopenia, autoimmune uveitis, Behcet's disease, blepharitis, bronchiectasis, bullous pemphigoid, catastrophic antiphospholipid syndrome, celiac disease, cervical spondylosis, chronic ischemia, cicatricial pemphigoid, clinical isolated syndrome with risk for multiple sclerosis, childhood onset psychiatric disorder, dacrocystitis, dermatomyositis, disc herniation, disc prolapse, drug induced immune hemolytic anemia, endophthalmitis, episcleritis, erythema multiforme, erythema multiforme major, gestational pemphigoid, Guillain-Barre syndrome, heart failure, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell hisiocytosis, livedo reticularis, microscopic polyangiitis, morbus bechterev, motor neuron disorders, mucous membrane pemphigoid, primary progressive multiple sclerosis, secondary progressive multiple sclerosis, relapsing remitting multiple sclerosis, multiple organ failure, myelodysplastic syndrome, nerve root disorder, neuropathy, Non-A Non-B hepatitis, osteolysis, ovarian cancer, pauciarticular JRA, peripheral artery occlusive disease (PAOD), peripheral vascular disease (PVD), peripheral artery disease, phlebitis, polychondritis, polymyalgia rheumatica, poliosis, polyarticular JRA, polyendocrine deficiency syndrome, polymyositis, post-pump syndrome, primary parkinsonism, prostatitis, psoratic arthropathy, pure red cell aplasia, primary adrenal insufficiency, Reiter's disease, recurrent neuromyelitis optica, rheumatic heart disease, SAPHO (synovitis, acne, pustulosis, hyperostosis, and osteitis), scleroderma, secondary amyloidosis, shock lung, sciatica, secondary adrenal insufficiency, septic arthritis, seronegative arthopathy, silicone associated connective tissue disease, Sneddon-Wilkinson Dermatosis, spondilitis ankylosans, Stevens-Johnson Syndrome, systemic inflammatory response syndrome, temporal arteritis, toxoplasmic retinitis, toxic epidermal necrolysis, TRAPS (Tumor Necrosis factor receptor), type 1 allergic reaction, type II diabetes, urticaria, usual interstitial pneumonia, vernal conjunctivitis, viral retinitis, Vogt-Koyanagi-Harada syndrome (VKH syndrome) and wet macular degeneration.

In a nineteenth embodiment the invention provides a method according to the nineteenth embodiment wherein the condition is selected from the group consisting of rheumatoid arthritis, osteoarthritis, asthma and multiple sclerosis.

In a twentieth embodiment the invention provides a pharmaceutical composition comprising a compound of Formula (I)

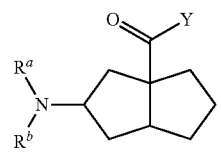

Formula (I)

and a pharmaceutically acceptable carrier or excipient, wherein $R^a$ is H or optionally substituted $(C_1-C_6)$alkyl;
$R^b$ is selected from the optionally substituted group consisting of —$(CH_2)_n$-aryl, —$CH(CH_3)$-aryl, —$(CH_2)_n$-aryl-aryl, —$(CH_2)_n$-aryl-heteroaryl, —$(CH_2)_n$—$(C_3$-

$C_8$)cycloalkyl, —$(CH_2)_n$-heteroaryl, —$(CH_2)_n$-heterocyclyl and —$(C_3$-$C_8)$cycloalkyl-aryl; or $R^a$ and $R^b$ are taken together with the nitrogen to form 2,3-dihydro-1H-isoindolyl, decahydroisoquinolinyl, optionally substituted piperidinyl or optionally substituted pyrrolidinyl;

Y is selected from the optionally substituted group consisting of 5,6,7,8-tetrahydro[1,6]naphthridinyl, —NH—$(CH_2)_n$-heterocycyl wherein the NH is attached to the carbonyl and -heterocyclyl-aryl wherein the heterocyclyl is attached to the carbonyl; and n is 0, 1 or 2.

DETAILED DESCRIPTION OF THE INVENTION

In a related aspect the invention provides a method for antagonizing CCR2 in a human subject suffering from a disorder in which CCR2 activity is detrimental, comprising administering to the human subject a compound of Formula (I)

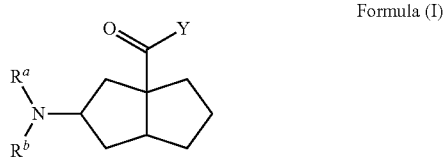

Formula (I)

such that CCR2 activity in the human subject is inhibited and treatment is achieved.

Many autoimmune diseases and disease associated with chronic inflammation, as well as acute responses, have been linked to activation of CCR2. The present compounds are useful in the treatment of inflammatory disorders including, but not limited to rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy and systemic lupus erythematosus.

The compounds of the invention are also useful in the treatment of cardiovascular disorders, such as acute myocardial infarction, acute coronary syndrome, chronic heart failure, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

A compound of Formula (I) or a pharmaceutically acceptable salt thereof or pharmaceutical compositions containing a therapeutically effective amount thereof is useful in the treatment of a disorder selected from the group comprising CNS system disorders, arthritis, rheumatoid arthritis, osteoarthritis, juvenile chronic arthritis, Lyme arthritis, psoriatic arthritis, reactive arthritis, and septic arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection (including but not limited to bone marrow and solid organ rejection), acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *Yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multisystem disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium* intracellulare, *mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as edema, ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as glomerulonephritis, diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, Crow- Fukase syndrome (POEMS), preeclampsia, menometrorrhagia, cat scratch fever, rubeosis, neovascular glaucoma and retinopathies such as those associated with diabetic retinopathy, retinopathy of prematurity, age-related macular degeneration or a central nervous system disorder. In addition, these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (I) of the invention can be used alone or in combination with another therapeutic agent to treat such diseases, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

For example, in the treatment or prevention of inflammation, the present compounds may be used in conjunction or combination with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as beta.2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib (Celebrex®) and rofecoxib (Vioxx®); (h) inhibitors of phosphodiesterase type IV (PDE-IV); (i) gold compounds such as auranofin and aurothioglucose, (j) inhibitors of phosphodiesterase type IV (PDE-IV); (k) other antagonists of the chemokine receptors, especially CCR1, CCR2, CCR3, CCR5, CCR6, CCR8 and CCR10; (l) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (m) anti-diabetic agents such as insulin, sulfonylureas, biguanides (metformin), α-glucosidase inhibitors (acarbose) and glitazones (troglitazone and pioglitazone); (n) preparations of interferon beta (interferon β-1α; interferon β-1b); (o) etanercept (Enbrel®), (p) antibody therapies such as orthoclone (OKT3), daclizumab (Zenapax®), infliximab (Remicade®), basiliximab (Simulect®) and anti-CD40 ligand antibodies (e.g., MRP-1); and (q) other compounds such as 5-aminosalicylic acid and pro-drugs thereof, hydroxychloroquine, D-penicillamine, antimetabolites such as azathioprene and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Immunosuppressants within the scope of the present invention further include, but are not limited to, leflunomide, RAD001, ERL080, FTY720, CTLA-4, antibody therapies such as orthoclone (OKT3), daclizumab (Zenapax®) and basiliximab (Simulect®), and antithymocyte globulins such as thymoglobulins.

In particularly preferred embodiments, the present methods are directed to the treatment or prevention of multiple sclerosis using a compound of the invention either alone or in combination with a second therapeutic agent selected from betaseron, avonex, azathioprene (Imurek®, Imuran®), capoxone, prednisolone and cyclophosphamide. When used in combination, the practitioner can administer a combination of the therapeutic agents, or administration can be sequential.

In still other particularly preferred embodiments, the present methods are directed to the treatment or prevention of rheumatoid arthritis, wherein the compound of the invention is administered either alone or in combination with a second therapeutic agent selected from the group consisting of methotrexate, sulfasalazine, hydroxychloroquine, cyclosporine A, D-penicillamine, infliximab (Remicade®), etanercept (Enbrel®), adalimumab (Humira®), auranofin and aurothioglucose.

In yet other particularly preferred embodiments, the present methods are directed to the treatment or prevention of an organ transplant condition wherein the compound of the invention is used alone or in combination with a second therapeutic agent selected from the group consisting of cyclosporine A, FK-506, rapamycin, mycophenolate, prednisolone, azathioprene, cyclophosphamide and an antilymphocyte globulin.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the CCR2 antagonists of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA®), (U.S. Pat. No. 6,090,382), CA2 (REMICADE™), CDP 571, and soluble p55 or p75 TNF receptors, derivatives, thereof, (p75TNFRIgG (ENBREL™) or p55TNFRIgG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SC10-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. IRAK, NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382; HUMIRA®), CA2 (REMICADE™), CDP 571, TNFR-Ig constructs, (p75TNFRIgG (ENBREL™) and p55TNFRIgG (LENERCEPT™)) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen Idec); anti-α4 antibody (Tysabri®; Biogen Idec); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (I) may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for angina with which a compound of Formula (I) of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril and bisoprolol fumarate.

Non-limiting examples of therapeutic agents for ankylosing spondylitis with which a compound of Formula (I) can be combined include the following: D2E7 (U.S. Pat. No. 6,090,382; HUMIRA®), ibuprofen, diclofenac, misoprostol, naproxen, meloxicam, indomethacin, diclofenac, celecoxib, rofecoxib, sulfasalazine, methotrexate, azathioprine, minocyclin, prednisone, etanercept, and infliximab.

Non-limiting examples of therapeutic agents for asthma with which a compound of Formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, co deine/promethazine, cefprozil, dexamethasone, guaifenesin/pseudoephedrine, chlorpheniramine/hydrocodone, nedocromil sodium, terbutaline sulfate, epinephrine, methylprednisolone and metaproterenol sulfate.

Non-limiting examples of therapeutic agents for COPD with which a compound of Formula (I) can be combined include the following: Letairs™ (ambrisentan), albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (I) can be combined include the following: Interferon-alpha-2a, Interferon-alpha-2b, Interferon-alpha con 1, Interferon-alpha-n1, pegylated interferon-alpha-2a, pegylated interferon-alpha-2b, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/nalact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of Formula (I) can be combined include the following: D2E7 (U.S. Pat. No. 6,090,382; HUMIRA®), methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of Formula (I) can be combined include the following: sirolimus, paclitaxel, everolimus, tacrolimus, ABT-578, and acetaminophen.

Non-limiting examples of therapeutic agents for sciatica with which a compound of Formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA®), CA2 (REMICADE™), CDP 571, TNFR-Ig constructs, (p75TNFRIgG (ENBREL™) and p55TNFRIgG (LENERCEPT™)).

In this invention, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Physiologically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I) and mixtures thereof.

Certain compounds of formula I may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —(CH$_2$)C(O)H or a moiety that contains a carboxylic acid) wherein the free hydrogen is replaced by (C$_1$-C$_4$)alkyl, (C$_2$-C$_{12}$)alkanoyloxymethyl, (C$_4$-C$_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl(such as (3-dimethylaminoethyl), carbamoyl-(C$_1$-C$_2$)alkyl, N,N-di(C$_1$-C$_2$)-alkylcarbamoyl-(C$_1$-C$_2$)alkyl and piperidino-, pyrrolidino- or morpholino(C$_2$-C$_3$) alkyl.

Other exemplary pro-drugs release an alcohol of Formula (I) wherein the free hydrogen of the hydroxyl substituent (e.g., R$^1$ contains hydroxyl) is replaced by (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylamino-methyl, succinoyl, (C$_1$-C$_6$)alkanoyl, α-amino(C$_1$-C$_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O(C$_1$-C$_6$)alkyl)$_2$ or glycosyl (the radical resulting from detachment of the hydroxyl of the hemiacetal of a carbohydrate).

The term "heterocyclic" or "heterocyclyl", as used herein, include non-aromatic, ring systems, including, but not limited to, monocyclic, bicyclic and tricyclic rings, which can be completely saturated or which can contain one or more units of unsaturation, (for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, morpholinyl, oxopiperidinyl, oxopyrrolidinyl, piperazinyl, piperidinyl, pyrrolidinyl, quinicludinyl, thiomorpholinyl, tetrahydropyranyl, tetrahydrofuranyl, 5,6, 7,8-tetrahydro[1,6]naphtyridinyl, decahydroisoquinolinyl and 2,3-dihydro-1H-isoindolyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo[b] thienyl, benzimidazolyl, benzofuranyl, benzoxazolyl, benzothiazolyl, benzothiadiazolyl, benzoxadiazolyl, furanyl, imidazolyl, imidazopyridyl, indolyl, indolinyl, indazolyl, isoindolinyl, isoxazole, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl or tropanyl.

When the term "substituted heterocyclic" (or heterocyclyl) or "substituted heteroaryl" is used, what is meant is that the heterocyclic group is substituted with one or more substituents that can be made by one of ordinary skill in the art and results in a molecule that is a CCR2 antagonist. For purposes of exemplification, which should not be construed as limiting the scope of this invention, preferred substituents for the heterocycle of this invention are each independently selected from the optionally substituted group consisting of alkenyl, alkoxy, alkoxyalkoxy, alkoxyalkyl, alkoxycarbonyl, alkoxycarbonylheterocycloalkoxy, alkyl, alkylcarbonyl, alkylester, alkyl-O—C(O)—, alkyl-heterocyclyl, alkyl-cycloalkyl, alkyl-nitrile, alkynyl, amido groups, amino, aminoalkyl, aminocarbonyl, carbonitrile, carbonylalkoxy, carboxamido, CF$_3$, CN, —C(O)OH, —C(O)H, —C(O)—C(CH$_3$)$_3$, —OH, —C(O)O-alkyl, —C(O)β-cycloalkyl, —C(O)O-heterocyclyl, —C(O)-alkyl, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxy, hydroxyalkyl, nitro, OCF$_3$, oxo, phenyl, —SO$_2$CH$_3$, —SO$_2$CR$_3$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocycloalkyl, cycloalkylalkyl, heterocyclothio, cycloalkylthio, —Z$^{105}$—C(O)N(R)$_2$, —Z$^{105}$—N(R)—C (O)—Z$^{200}$, —Z$^{105}$—N(R)—S(O)$_2$—Z$^{200}$, —Z$^{105}$—N(R)—C(O)—N(R)—Z$^{200}$, —N(R)—C(O)R, —N(R)—C(O)OR, OR—C(O)-heterocyclyl-OR, R$_c$ and —CH$_2$OR$_c$;

wherein R$_3$ is C$_1$-C$_4$ alkyl, C$_3$-C$_6$ cycloalkyl or phenyl;

wherein p is 0, 1 or 2;

where R$_c$ for each occurrence is independently hydrogen, optionally substituted alkyl, optionally substituted aryl, —(C$_1$-C$_6$)—NR$_d$R$_e$, -E-(CH$_2$)$_t$—NR$_d$R$_e$, -E-(CH$_2$)$_t$—O-alkyl, -E-(CH$_2$)$_t$—S-alkyl, or -E-(CH$_2$)$_t$—OH;

wherein t is an integer from about 1 to about 6;

Z$^{105}$ for each occurrence is independently a covalent bond, alkyl, alkenyl or alkynyl; and Z$^{200}$ for each occurrence is independently selected from an optionally substituted group selected from the group consisting of alkyl, alkenyl, alkynyl, phenyl, alkyl-phenyl, alkenyl-phenyl or alkynyl-phenyl;

E is a direct bond, O, S, S(O), S(O)$_2$, or NR$_f$, wherein R$_f$ is H or alkyl and R$_d$ and R$_e$ are independently H, alkyl, alkanoyl or SO$_2$-alkyl; or R$_d$, R$_e$ and the nitrogen atom to which they are attached together to form a five- or six-membered heterocyclic ring.

An "heterocycloalkyl" group, as used herein, is a heterocyclic group that is linked to a compound by an aliphatic group having from one to about eight carbon atoms. For example, a heterocycloalkyl group is a morpholinomethyl group.

As used herein, "alkyl" means C$_1$-C$_8$ and includes straight chained or branched hydrocarbons, which are completely saturated. Preferred alkyls are methyl, ethyl, propyl, isopropyl, butyl, t-butyl, pentyl, hexyl and isomers thereof. As used herein, "alkenyl" and "alkynyl" means C$_2$-C$_8$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, cycloalkyl means C$_3$-C$_{12}$ monocyclic or multicyclic (e.g., bicyclic, tricyclic, etc.) hydrocarbons that is completely saturated or has one or more unsaturated bonds but does not amount to an aromatic group. Preferred examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—$C_1$-$C_6$-alkyl-OR, —O—$C_1$-$C_6$-alkyl-N(R)$_2$, and OCF$_3$), alkoxyalkoxy, alkoxycarbonyl, alkoxycarbonylpiperidinyl-alkoxy, alkyl groups (which itself can also be substituted, such as —$C_1$-$C_6$-alkyl-OR, —$C_1$-$C_6$-alkyl-N(R)$_2$, and —CF$_3$), alkylamino, alkylcarbonyl, alkylester, alkylnitrile, alkylsulfonyl, amino, aminoalkoxy, CF$_3$, COH, COON, CN, cycloalkyl, dialkylamino, dialkylaminoalkoxy, dialkylaminocarbonyl, dialkylaminocarbonylalkoxy, dialkylaminosulfonyl, esters (—C(O)—OR, where R is groups such as alkyl, heterocycloalkyl (which can be substituted), heterocyclyl, etc., which can be substituted), halogen or halo group (F, Cl, Br, I), hydroxy, morpholinoalkoxy, morpholinoalkyl, nitro, oxo, OCF$_3$, optionally substituted phenyl, S(O)$_2$CH$_3$, S(O)$_2$CF$_3$, and sulfonyl, N-alkylamino or N,N-dialkylamino (in which the alkyl groups can also be substituted).

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given CCR2 activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit CCR2 signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the CCR2 modulating effects, or minimal effective concentration (MEC). The MEC will vary for each compound but can be estimated from in vitro data; e.g. the concentration necessary to achieve 50-90% inhibition of CCR2 using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

Parts by weight

| | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

A further aspect of the present invention provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

The teachings of all references, including journal articles, patents and published patent applications, are incorporated herein by reference in their entirety.

Enzyme Assays

Assays for Screening Compounds of Formula (I)

The in vitro potency of compounds in antagonizing CCR2 discussed herein or described in the art may be determined by the procedures detailed below.

CHO cells expressing either human CCR2b or murine CCR2 were generated as follows. cDNA for human CCR2b (cloned from human blood) and murine CCR2 (cloned from mouse brain or PEC) were cloned into plasmid pcDNA3.1 (from Invitrogen). The resulting plasmids were separately transfected into CHO cells expressing human Ga16 (from Molecular Devices). Sequences of the transfected CCR2 open reading frames in the resulting cell lines were identical to human CCR2b (NM_000648) and mouse CCR2 (NM_00915.1) respectively.

Inhibition of MCP-1 Binding to hCCR2 or mCCR2

Radioligand binding assays were performed in CHO cells expressing either human CCR2B and the $G\alpha_{16}$ coupling protein or murine CCR2 and the $G\alpha_{16}$ coupling protein. All compounds were dissolved in DMSO and assays run at a final DMSO concentration of 1% (v/v). [$^{125}$I]-labeled human and murine MCP-1 was purchased from PerkinElmer. Unlabeled human and murine MCP-1 were purchased from Peprotech. Assays with cells expressing human CCR2B were performed with human MCP-1, while assays with cells expressing murine CCR2 were performed with murine MCP-1.

Compounds are serially diluted in DMSO before diluting into assay buffer (25 mM HEPES, pH 7.4, 5 mM $MgCl_2$, 1 mM $CaCl_2$, 0.5% BSA) with cryo preserved CHO cells expressing either human CCR2B and the $G\alpha_{16}$ coupling protein or murine CCR2 and the $G\alpha_{16}$ coupling protein ($50\times10^3$/well) and [$^{125}$I]-MCP-1 (50 pM for human CCR2, 100 pM for murine CCR2). The reaction was incubated at room temperature for 90 minutes before transferring to GF/C filter plates (PerkinElmer) pre-treated with 0.3% polyethyleneimine for 2 hours at 4° C. The filter plates are washed six times with ice cold wash buffer (25 mM HEPES, pH 7.4, 5 mM $MgCl_2$, 1 mM $CaCl_2$, 500 mM NaCl) and dried before adding 50 ul/well Microscint to each well. Plates are counted on Packard Topcount scintillation counter where background binding is determined 100 nM MCP-1 and control total binding determined by addition of DMSO in place of the test compound. The radioactivity values (cpm) were used to calculate the percent inhibition at a given compound concentration and the data fit to a sigmoidal curve in a semi-log plot to determine $IC_{50}$ values.

Inhibition of MCP-1-Induced Intracellular Calcium Release in Cells Expressing hCCR2 or mCCR2

Calcium flux assays were performed in CHO cells expressing either human CCR2B and the $G\alpha_{16}$ coupling protein or murine CCR2 and the $G\alpha_{16}$ coupling protein. All compounds were dissolved in DMSO and assays run at a final DMSO concentration of 1% (v/v). Human and murine MCP-1 were purchased from Peprotech and used at a final assay concentration of 10 nM. Assays with cells expressing human CCR2B were performed with human MCP-1, while assays with cells expressing murine CCR2 were performed with murine MCP-1.

Briefly, cells were cultured overnight in a microtiter plate at 40,000 per well. The next day, the resultant adherent cells were incubated in assay buffer (20 mM HEPES pH 7.4, 0.1% bovine serum albumin, and 2.5 mM Probenocid in Hank's Buffered Saline Solution) containing 5 µg/ml µM Fluo-4 dye (Molecular Probes) at room temperature for 60 min. The dye-containing assay buffer was removed and replace by assay buffer without dye. Calcium flux assays were performed on a FLIPR Tetra instrument (Molecular Devices) by adding compound to the cells followed by addition of MCP-1 and measuring the change in fluorescence as a function of time. Maximal and minimal values for fluorescence were determined using 100 nM MCP-1 and buffer addition, respectively. Fluorescence values were used to calculate the percent inhibition at a given compound concentration and the data fit to a sigmoidal curve in a semi-log plot to determine $IC_{50}$ values.

Compounds of the invention may be prepared using the synthetic scheme illustrated in Scheme A. Starting materials are commercially available or may be prepared by the procedures described herein or by procedures that would be well known to one skilled in the art of organic chemistry. The variables used in the Scheme are as defined herein or as in the claims. General procedures are noted in parentheses.

Scheme A

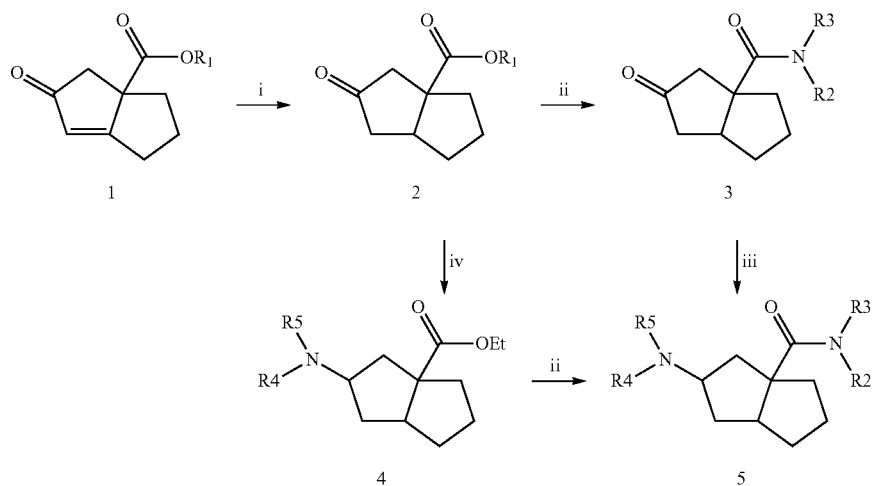

A method for preparing 2-aminooctahydropentalene-3a-carboxamide compounds of the invention is illustrated in Scheme A. In Scheme A, step i, a suitably substituted 4,5,6,6a-tetrahydropentalen-2(1H)-one 1 is hydrogenated, typically in the presence of hydrogen and a metal catalyst (such as Pd/C) in an organic solvent (such as EtOH). Ester hydrolysis, typically conducted in an organic solvent such as THF treated with aqueous sodium hydroxide, followed by amide coupling with a suitable amine (step ii) provides intermediate 3. The amide coupling reaction of the ketone with a suitably substituted amine is typically run in an organic solvent (such as DMA) in the presence of a base (such as $Et_3N$), and activating agent (such as HOBT), and a coupling reagent (such as PS-carbodiimide) at ambient temperature. The reductive amination reaction (steps iii or iv) is typically conducted in an organic solvent (such as 1,2-dichloroethane) at room temperature with sodium triacetoxyborohydride and acetic acid. Ester 4 is functionalized utilizing chemistry similar to that described above in step (ii) to afford product 5. Product 5 can then be isolated and purified using standard techniques (such as crystallization, flash column chromatography, or reverse-phase liquid chromatography).

ABBREVIATIONS

| | |
|---|---|
| DCE | Dichloroethane |
| DCM | Dichloromethane |
| DMA | N,N-Dimethylacetamide |
| DMSO | Dimethyl sulfoxide |
| $Et_3N$ | Triethylamine |
| $Et_2O$ | Diethyl ether |
| HOBT | 1-Hydroxybenzotriazole |
| HPLC | High Performance Liquid Chromatography |
| MeCN | Acetonitrile |
| MeOH | Methanol |
| $MgSO_4$ | Magnesium sulfate |
| i-PrOH | 2-Propanol |
| n-PrOH | 1-Propanol |
| PS-carbodiimide | N-Cyclohexylcarbodiimide-N'-propyloxymethyl polystyrene |
| RP | Reverse Phase |
| $R_t$ | Retention time |
| THF | Tetrahydrofuran |

Synthetic Details

Analytical data are included either in the illustrations of the general procedures or in the tables of examples. Unless otherwise stated, all $^1H$ or $^{13}C$ NMR data were collected on a Varian Mercury Plus 400 MHz instrument; chemical shifts are quoted in parts per million (ppm). High pressure liquid chromatography (HPLC) analytical data are either detailed within the experimental or referenced to the table of HPLC conditions, using the lower case method letter, in Table A.

TABLE A

List of HPLC methods

| Method | HPLC Conditions<br>Unless indicated otherwise mobile phase A was 10 mM ammonium acetate, mobile phase B was HPLC grade acetonitrile. |
|---|---|
| a | 5-95% B over 3.7 min with a hold at 95% B for 1 min (1.3 mL/min flow rate). 4.6 × 50 mm Waters Atlantis dC18 column (5 μm particles). Detection methods are diode array (DAD) and evaporative light scattering (ELSD) detection as well as pos/neg electrospray ionization. |
| b | 5-60% B over 1.5 min then 60-95% B to 2.5 min with a hold at 95% B for 1.2 min (1.3 mL/min flow rate). 4.6 × 30 mm Vydac Genesis C8 column (4 μm particles). Detection methods are diode array (DAD) and evaporative light scattering (ELSD) detection as well as pos/neg electrospray ionization. |
| c | 5-95% B in 3.7 min with a hold at 95% B for 1 min (1.3 mL/min flow rate). 4.6 × 50 mm Waters Atlantis dC18 column (5 μm particles). Detection methods are diode array (DAD) and evaporative light scattering (ELSD) detection as well as pos/neg atmospheric pressure chemical ionization (APCI) |
| d | 10 to 70% gradient over 19 min of isopropanol in heptane with 0.2% diethylamine on Daicel AD-H column (4.6 × 250 mm) at 35 deg C. and 1.0 mL/min flow rate (UV wavelength monitored = 265 nm) |

GENERAL PROCEDURES AND EXAMPLES

The general synthetic schemes that were utilized to construct the majority of compounds disclosed in this application are described below in Schemes 1-2.

Scheme 1. General synthetic route to octahydropentalene-3a-carboxamides(General procedure A, B)

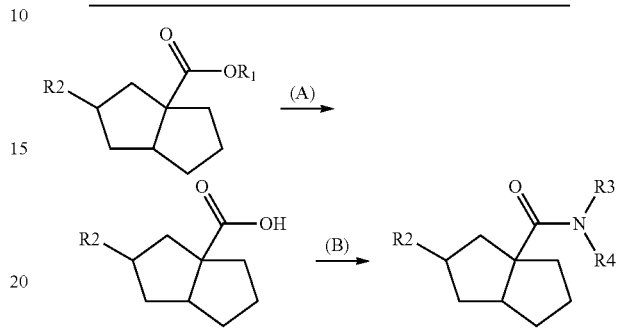

Scheme 2. General synthetic route to 2-aminooctahydropentalenes (General procedure C)

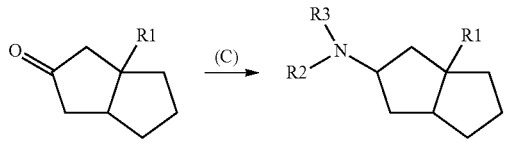

List of General Procedures:

General Procedure A: Hydrolysis of an ester to a carboxylic acid.

General Procedure B: Formation of an amide by peptide coupling.

General Procedure C: Formation of an amine by reductive amination.

Intermediates:

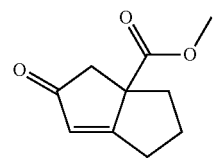

Methyl 5-oxo-1,2,3,3a,4,5-hexahydropentalene-3a-carboxylate was prepared via the route detailed in J. Org. Chem. 1981, 46, 2816-2818.

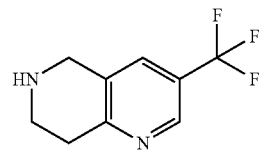

3-Trifluoromethyl-5,6,7,8-tetrahydro-[1,6]naphthyridine was prepared via the route detailed in WO 2005/044264.

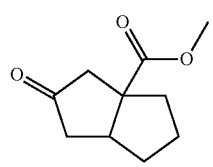

Methyl 2-oxooctahydropentalene-3a-carboxylate: Methyl 5-oxo-1,2,3,3a,4,5-hexahydropentalene-3a-carboxylate (2.5 g, 12.8 mmol) in ethanol (25 mL) was purged with nitrogen for about 10 minutes with stirring. Palladium on carbon (0.043 g, 20 mol %) was added and the reaction vessel was purged with nitrogen for about 10 minutes. The flow of nitrogen was stopped and the flask was flushed with hydrogen. The reaction mixture was stirred overnight under an atmosphere of hydrogen. The flask was flushed with nitrogen for about 20 minutes. The reaction mixture was passed through a pad of Celite® and the filtrate was concentrated in vacuo. The residue was purified by flash column chromatography (eluting with 25% ethyl acetate/heptane) to afford ethyl 2-oxooctahydropentalene-3a-carboxylate (2.04 g, 10.4 mmol, 81%).

The general procedure letter codes constitute a synthetic route to the final product. A worked example of how the route is determined is given below using the synthesis of Preparation #3 as a non-limiting illustration. Preparation #3 ([2-(2,4-Dimethyl-benzylamino)-hexahydro-pentalen-3a-yl]-(3-trifluoromethyl-7,8-dihydro-5H-[1,6]naphthyridin-6-yl)-methanone) was prepared from 2-(2,4-dimethylbenzylamino)octahydropentalene-3a-carboxylic acid and 3-(trifluoromethyl)-5,6,7,8-tetrahydro-1,6-napthyridine using General Procedure B, as represented in the following synthetic scheme.

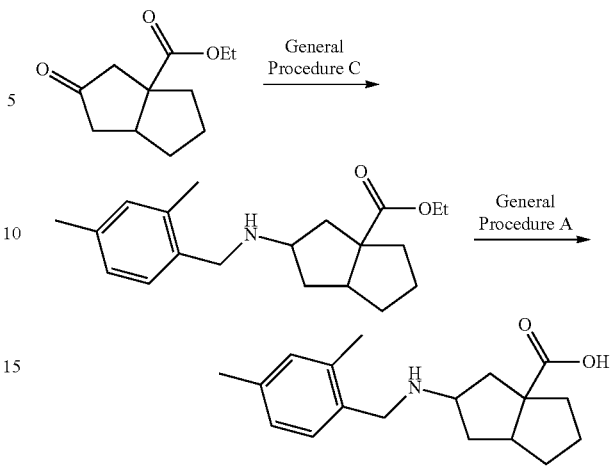

General Procedure A: Hydrolysis of an Ester to a Carboxylic Acid.

To a mixture of an ester (1 equivalent) in an organic solvent (preferably THF) is added an aqueous solution of inorganic hydroxide (1-30 equivalents, preferably about 10 equivalents) (preferably sodium hydroxide). The reaction mixture is stirred at about 20-50° C. (preferably at about 25° C.) for about 1-24 h (preferably about 18 h). The solvent is removed under reduced pressure and the residue is partitioned between an organic solvent (preferably DCM) and water then separated and dried over dessicant (preferably magnesium sulfate) and concentrated. The crude product can be further purified by chromatography or crystallization or used without additional purification.

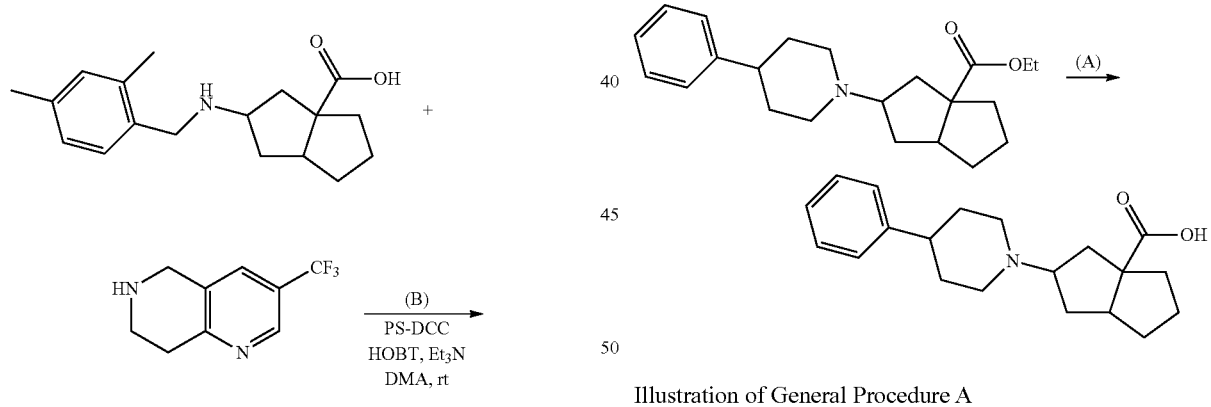

Illustration of General Procedure A

Preparation #1

2-(4-Phenyl-piperidin-1-yl)-hexahydro-pentalene-3a-carboxylic acid

To a solution of ethyl 2-(4-phenylpiperidin-1-yl)octahydropentalene-3a-carboxylate (1.85 g, 5.42 mmol) in THF (35 mL) was added a solution of sodium hydroxide (2.16 g, 54.2 mmol) in water (35 mL). The reaction mixture was stirred at ambient temperature for about 18 h. The solvent was removed under reduced pressure and the crude product was extracted into DCM (3×20 mL). The combined organic phases were washed with water (3×50 mL) and dried over MgSO$_4$. Concentration in vacuo gave 2-(4-phenyl-piperidin-1-yl)-

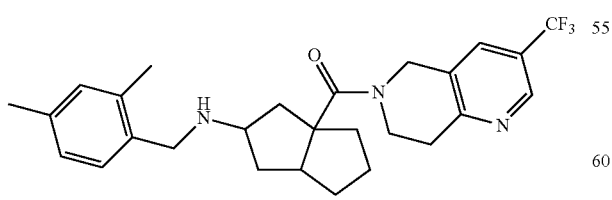

The acid was prepared using the route (C, A). This translates into the following sequence, where the acid starting material used in general procedure B is the product of the following procedures C and A, in the given order.

hexahydro-pentalene-3a-carboxylic acid (1.70 g) that was used in the next step without further purification.

General Procedure B: Formation of an Amide by Peptide Coupling.

A mixture of an acid (1 equivalent), a suitably substituted amine (1-5 equivalents, preferably 1 equivalent), a coupling reagent (1-10 equivalents, preferably 1.5 equivalents, preferably PS-carbodiimide), an activating reagent (1-3 equivalents, preferably 1 equivalent, preferably HOBT) and a base (1-10 equivalents, preferably 1 equivalent, preferably Et$_3$N) in an organic solvent (preferably DMA) is stirred at about 20-50° C. (preferably at about 25° C.) for about 1-72 h (preferably about 48 h). The resin is removed by filtration and the solvent is removed under reduced pressure. The crude product can be further purified by chromatography or crystallization.

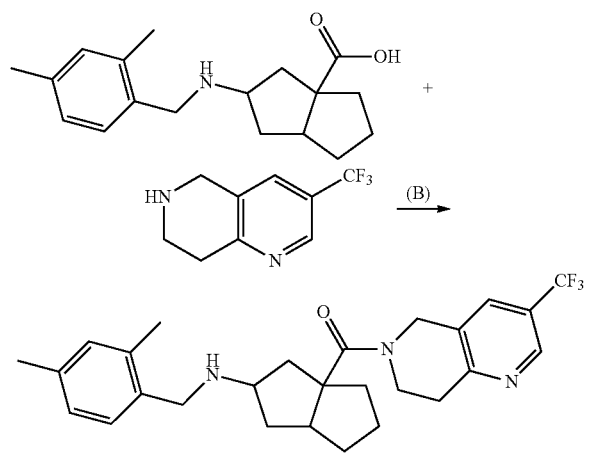

Illustration of General Procedure B

Preparation #2

{2-[(2,4-Dimethyl-benzyl)-amino]-hexahydro-pentalen-3a-yl}-(3-trifluoro-methyl-7,8-dihydro-5H-[1,6]naphthyridin-6-yl)-methanone A mixture of 2-((2,4-dimethylbenzyl)(methyl)amino)octahydropentalene-3a-carboxylic acid (0.075 g, 0.25 mmol), 3-(trifluoromethyl)-5,6,7,8-tetrahydro-1,6-naphthyridine (0.050 g, 0.25 mmol), N-((3-(4-methylbenzyloxy)propylimino)methylene)cyclohexanamine (resin bound, 1.42 mmol/g, 0.262 g, 0.373 mmol), 1H-benzo[d][1,2,3]triazol-1-ol (0.034 g, 0.25 mmol) and triethylamine (0.025 g, 0.25 mmol) in DMA (3.1 mL) was stirred at ambient temperature for about 48 h. The resin was removed by filtration and the solvent removed under reduced pressure. The crude material was purified by RP-HPLC to provide {2-[(2,4-dimethyl-benzyl)-methyl-amino]-hexahydro-pentalen-3a-yl}-(3-trifluoro-methyl-7,8-dihydro-5H-[1,6]naphthyridin-6-yl)-methanone (0.026 g). RP-HPLC (Table A, Method b) R$_t$ 1.78 min; m/z: (M+H)$^+$472.

General Procedure C: Formation of an Amine by Reductive Amination.

To a solution of ketone (1 equivalent) in an organic solvent (preferably DCE) is added an amine (1-5 equivalents, preferably 1 equivalent) and the mixture is stirred at about 20-50° C. (preferably at about 25° C.) for about 1-72 h (preferably about 2 h) then a reducing agent (1-10 equivalents, preferably about 1.5 equivalents, preferably sodium triacetoxyborohydride) with or without an acid additive (about 1-5 equivalents, preferably about 1.5 equivalents, preferably acetic acid) are added. The mixture is then stirred at about 20-50° C. (preferably at about 25° C.) for about 1-72 h (preferably about 18 h). The reaction is quenched by the addition of an aqueous base (preferably aqueous sodium bicarbonate) and then partitioned with an organic solvent (preferably DCM). The solvent is removed under reduced pressure. The crude product can be further purified by chromatography or crystallization.

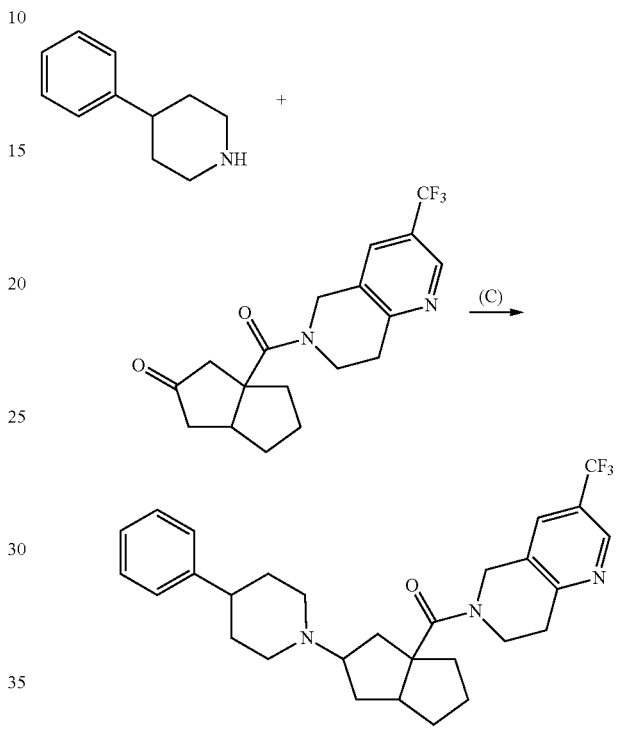

Illustration of General Procedure C

Preparation #3

[2-(4-Phenyl-piperidin-1-yl)-hexahydro-pentalen-3a-yl]-(3-trifluoromethyl-7,8-dihydro-5H-[1,6]naphthyridin-6-yl)-methanone To a solution of 3a-(3-(trifluoromethyl)-5,6,7,8-tetrahydro-1,6-naphthyridine-6-carbonyl)hexahydropentalen-2(1H)-one (0.175 g, 0.497 mmol) in DCE (4.3 mL) was added 4-phenylpiperidine (0.080 g, 0.50 mmol). The reaction mixture was stirred at ambient temperature for about 2 h then sodium triacetoxyborohydide (0.158 g, 0.745 mmol) and acetic acid (0.043 mL, 0.74 mmol) were added. The reaction mixture was then stirred at ambient temperature for about 18 h. Saturated aqueous sodium bicarbonate was added to the reaction mixture and the product was extracted into DCM (3×10 mL). The solvent was removed under reduced pressure and the crude material was purified by RP-HPLC to provide [2-(4-phenyl-piperidin-1-yl)-hexahydro-pentalen-3a-yl]-(3-trifluoromethyl-7,8-dihydro-5H-[1,6]naphthyridin-6-yl)-methanone as a mixture of four diastereomers (0.075 g). RP-HPLC (Table A, Method c) R$_t$ 2.05 min; m/z: (M+H)$^+$ 498. In addition, the diastereomers were separated using a two-step chiral HPLC method (Step 1: Diastereomer separation: Isocratic using 85% heptane, 7.5% methanol, 7.5% ethanol with 0.2% diethylamine on a Daicel OD-H column (20× 250 mm) at 35 deg C. and 12 mL/min flow rate (UV wavelength monitored=265 nm). Step 2: Enantiomer separation: 10-70% gradient over 19 min of isopropanol in heptane with 0.2% diethylamine on a Daicel AD-H column (20×250 mm) at 35 deg C. and 16 ml/min flow rate (UV wavelength monitored=265 nm)) to provide the four enantiomers—the absolute configuration of each compound was not determined Isomer 1: RP-HPLC (Table A, Method d) $R_t$ 12.66 min. Isomer 2: RP-HPLC (Table A, Method d) $R_t$ 13.57 min. Isomer 3: RP-HPLC (Table A, Method d) $R_t$ 8.46 min Isomer 4: RP-HPLC (Table A, Method d) $R_t$ 11.76 min.

TABLE 1

Examples synthesized using general procedure B

| Amine | Core | Product | Ex. # | HPLC $R_t$ (Method) | m/z or $^1$H NMR (d6 DMSO, 400 MHz) |
|---|---|---|---|---|---|
| 3-(trifluoromethyl)-5,6,7,8-tetrahydro-1,6-naphthyridine | 2-(methyl(tetrahydro-2H-pyran-4-yl)amino)octahydropentalene-3a-carboxylic acid (C, A) | | 1.1 | 1.57 min (b) | (M + H)$^+$ 452 |
| 1-(4-(trifluoromethyl)phenyl)piperazine | 2-(methyl(tetrahydro-2H-pyran-4-yl)amino)octahydropentalene-3a-carboxylic acid (C, A) | | 1.2 | 1.88 min (b) | (M + H)$^+$ 480 |
| 2-(pyrrolidin-1-yl)ethanamine | 2-(methyl(tetrahydro-2H-pyran-4-yl)amino)octahydropentalene-3a-carboxylic acid (C, A) | | 1.3 | 0.82 min (b) | (M + H)$^+$ 364 |
| 3-(trifluoromethyl)-5,6,7,8-tetrahydro-1,6-naphthyridine | 2-(methyl(2-(piperidin-1-yl)ethyl)amino)octahydropentalene-3a-carboxylic acid (C, A) | | 1.4 | 1.45 min (b) | (M + H)$^+$ 479 |
| 3-(trifluoromethyl)-5,6,7,8-tetrahydro-1,6-naphthyridine | 2-[(2,4-dimethylbenzyl)-methylamino]-hexahydropentalene-3a-carboxylic acid (C, A) | | 1.5 | 2.06 min (c) | (M + H)$^+$ 486 |

TABLE 2

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| (2,4-dimethyl-benzyl)-methylamine | 3a-[4-(3-trifluoromethyl-phenyl)-piperazine-1-carbonyl]-hexahydro-pentalen-2-one (A, B) | | 2.1 | 2.32 min (a) | (M + H)$^+$ 514 |
| 4-phenyl-piperidine | 3a-[4-(3-trifluoromethyl-phenyl)-piperazine-1-carbonyl]-hexahydro-pentalen-2-one (A, B) | | 2.2 | 2.29 min (a) | (M + H)$^+$ 526 |
| 4-phenyl-cyclohexyl-amine | 3a-[4-(3-trifluoromethyl-phenyl)-piperazine-1-carbonyl]-hexahydro-pentalen-2-one (A, B) | | 2.3 | 2.45 min (a) | (M + H)$^+$ 540 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| (tetrahydro-pyran-4-yl)-methylamine | 3a-[4-(3-trifluoromethyl-phenyl)-piperazine-1-carbonyl]-hexahydro-pentalen-2-one (A, B) | 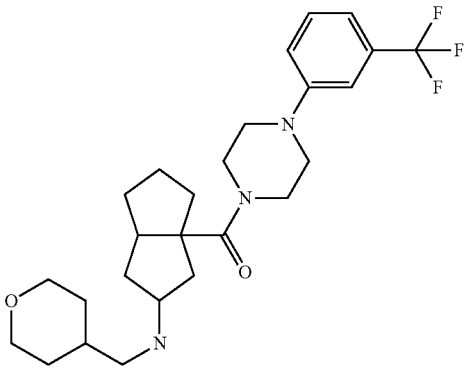 [SMILES: O=C(N1CCN(c2cccc(C(F)(F)F)c2)CC1)C12CCCC1CC(NCC1CCOCC1)C2] | 2.4 | 1.89 min (a) | (M + H)$^+$ 480 |
| 2,3-dihydro-1H-isoindole | 3a-(3-(trifluoromethyl)-5,6,7,8-tetrahydro-1,6-naphthyridine-6-carbonyl)hexahydro-pentalen-2(1H)-one (A, B) | 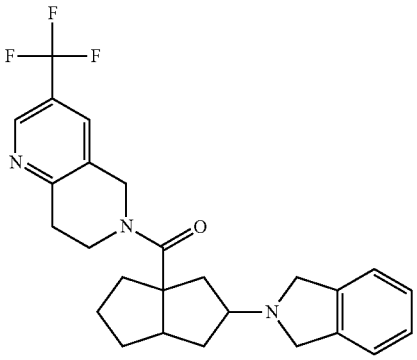 [SMILES: O=C(N1CCc2ncc(C(F)(F)F)cc2C1)C12CCCC1CC(N1Cc3ccccc3C1)C2] | 2.5 | 1.78 min (a) | (M + H)$^+$ 456 |
| 4-fluoro-benzylamine | 3a-(3-(trifluoromethyl)-5,6,7,8-tetrahydro-1,6-naphthyridine-6-carbonyl)hexahydro-pentalen-2(1H)-one (A, B) | 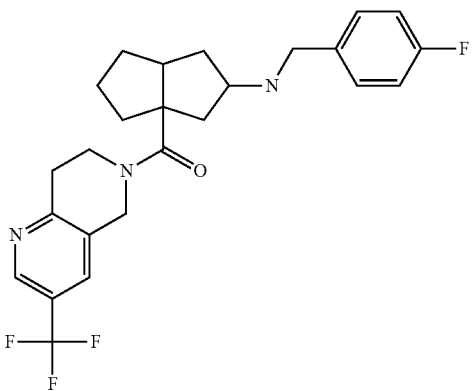 [SMILES: O=C(N1CCc2ncc(C(F)(F)F)cc2C1)C12CCCC1CC(NCc1ccc(F)cc1)C2] | 2.6 | 1.81 min (a) | (M + H)$^+$ 462 |

TABLE 2-continued

Examples synthesized using general procedure C

| Amine | Core | Product | Ex. # | HPLC R_t (Method) | m/z or ¹H NMR (d6 DMSO, 400 MHz) |
|---|---|---|---|---|---|
| 2-fluoro-benzylamine | 3a-(3-(trifluoromethyl)-5,6,7,8-tetrahydro-1,6-naphthyridine-6-carbonyl)hexahydro-pentalen-2(1H)-one (A, B) | 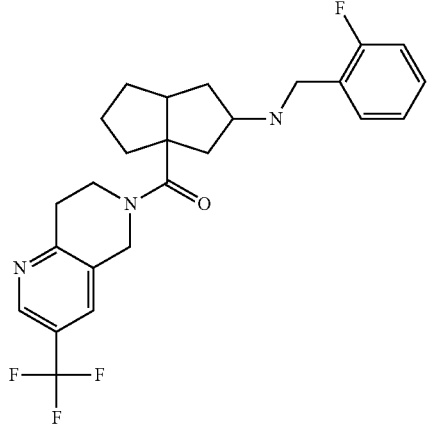 [SMILES: O=C(N1CCc2ncc(C(F)(F)F)cc2C1)C12CCCC1CC(NCc1ccccc1F)C2] | 2.7 | 1.77 min (a) | (M + H)⁺ 462 |
| 4-aminomethyl-benzonitrile | 3a-(3-(trifluoromethyl)-5,6,7,8-tetrahydro-1,6-naphthyridine-6-carbonyl)hexahydro-pentalen-2(1H)-one (A, B) | 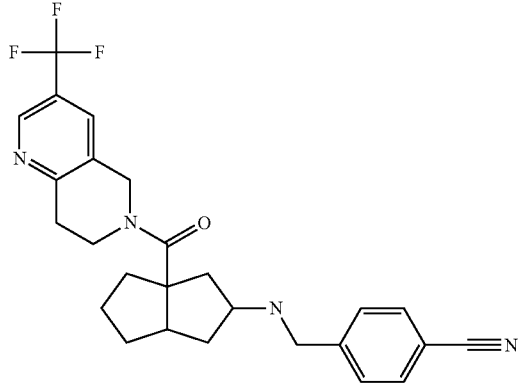 [SMILES: N#Cc1ccc(CNC2CC3CCCC3(C(=O)N3CCc4ncc(C(F)(F)F)cc4C3)C2)cc1] | 2.8 | 1.75 min (a) | (M + H)⁺ 469 |
| indan-1-yl-amine | 3a-(3-(trifluoromethyl)-5,6,7,8-tetrahydro-1,6-naphthyridine-6-carbonyl)hexahydro-pentalen-2(1H)-one (A, B) | 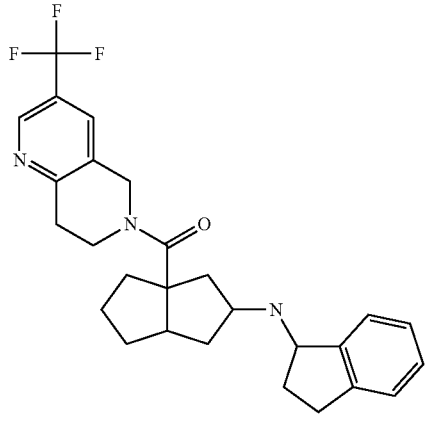 [SMILES: O=C(N1CCc2ncc(C(F)(F)F)cc2C1)C12CCCC1CC(NC1CCc3ccccc31)C2] | 2.9 | 1.83 min (a) | (M + H)⁺ 470 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 3,4-dimethyl-benzylamine | 3a-(3-(trifluoromethyl)-5,6,7,8-tetrahydro-1,6-naphthyridine-6-carbonyl)hexahydropentalen-2(1H)-one (A, B) | | 2.10 | 1.93 min (a) | (M + H)$^+$ 472 |
| 2,5-dimethyl-benzylamine | 3a-(3-(trifluoromethyl)-5,6,7,8-tetrahydro-1,6-naphthyridine-6-carbonyl)hexahydropentalen-2(1H)-one (A, B) | | 2.11 | 1.93 min (a) | (M + H)$^+$ 472 |
| 2-methoxy-benzylamine | 3a-(3-(trifluoromethyl)-5,6,7,8-tetrahydro-1,6-naphthyridine-6-carbonyl)hexahydropentalen-2(1H)-one (A, B) | | 2.12 | 1.83 min (a) | (M + H)$^+$ 474 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 3-methoxy-benzylamine | 3a-(3-(trifluoromethyl)-5,6,7,8-tetrahydro-1,6-naphthyridine-6-carbonyl)hexahydro-pentalen-2(1H)-one (A, B) | 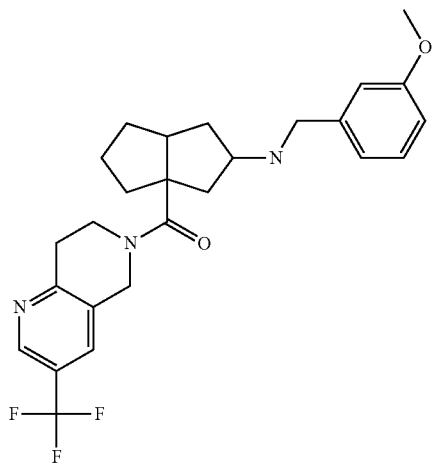 [SMILES: COc1cccc(CNC2CC3CCCC3(C(=O)N3CCc4ncc(C(F)(F)F)cc4C3)C2)c1] | 2.13 | 1.79 min (a) | (M + H)$^+$ 474 |
| 4-methoxy-benzylamine | 3a-(3-(trifluoromethyl)-5,6,7,8-tetrahydro-1,6-naphthyridine-6-carbonyl)hexahydro-pentalen-2(1H)-one (A, B) | 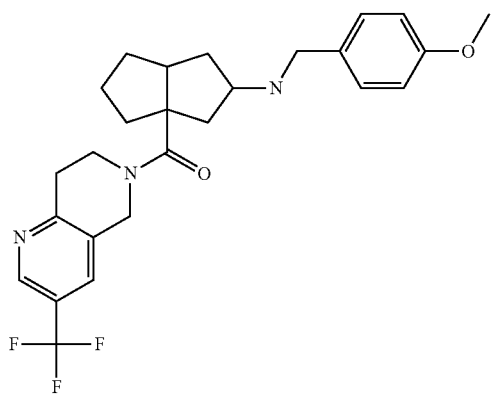 [SMILES: COc1ccc(CNC2CC3CCCC3(C(=O)N3CCc4ncc(C(F)(F)F)cc4C3)C2)cc1] | 2.14 | 1.85 min (a) | (M + H)$^+$ 474 |
| 3-chloro-benzylamine | 3a-(3-(trifluoromethyl)-5,6,7,8-tetrahydro-1,6-naphthyridine-6-carbonyl)hexahydro-pentalen-2(1H)-one (A, B) | 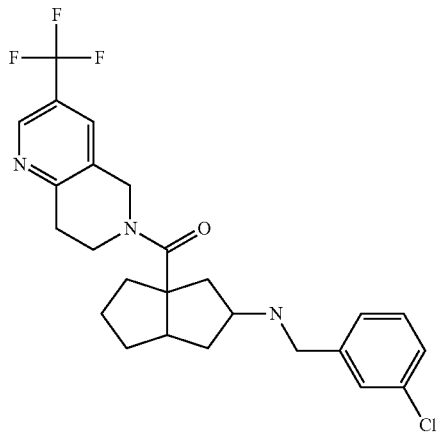 [SMILES: O=C(N1CCc2ncc(C(F)(F)F)cc2C1)C12CCCC1CC(NCc1cccc(Cl)c1)C2] | 2.15 | 1.93 min (a) | (M + H)$^+$ 478 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 4-chloro-benzylamine | 3a-(3-(trifluoromethyl)-5,6,7,8-tetrahydro-1,6-naphthyridine-6-carbonyl)hexahydropentalen-2(1H)-one (A, B) | 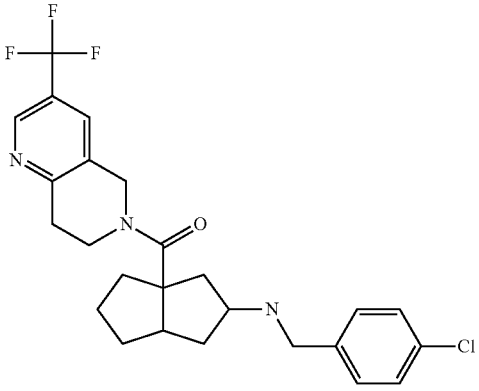 [SMILES: O=C(N1CCc2ncc(C(F)(F)F)cc2C1)C12CCCC1CC(NCc1ccc(Cl)cc1)C2] | 2.16 | 1.9 min (a) | (M + H)$^+$ 478 |
| 1,2,3,4-tetrahydro-naphthalen-1-ylamine | 3a-(3-(trifluoromethyl)-5,6,7,8-tetrahydro-1,6-naphthyridine-6-carbonyl)hexahydropentalen-2(1H)-one (A, B) | 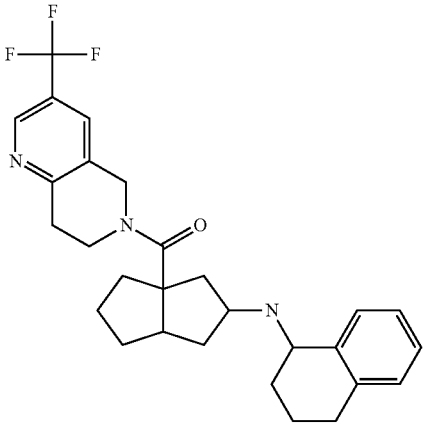 [SMILES: O=C(N1CCc2ncc(C(F)(F)F)cc2C1)C12CCCC1CC(NC1CCCc3ccccc31)C2] | 2.17 | 1.96 min (a) | (M + H)$^+$ 484 |
| (3-aminomethyl-phenyl)-dimethyl-amine | 3a-(3-(trifluoromethyl)-5,6,7,8-tetrahydro-1,6-naphthyridine-6-carbonyl)hexahydropentalen-2(1H)-one (A, B) | 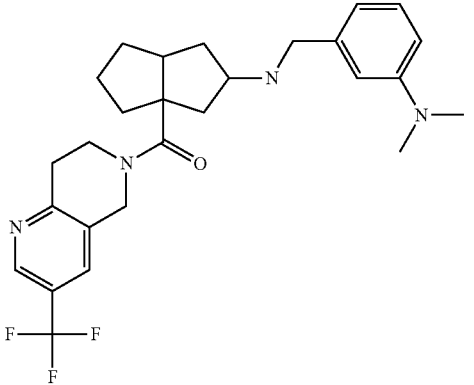 [SMILES: CN(C)c1cccc(CNC2CC3CCCC3(C(=O)N3CCc4ncc(C(F)(F)F)cc4C3)C2)c1] | 2.18 | 1.88 min (a) | (M + H)$^+$ 487 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| N-(4-aminomethyl-phenyl)-acetamide | 3a-(3-(trifluoromethyl)-5,6,7,8-tetrahydro-1,6-naphthyridine-6-carbonyl)hexahydro-pentalen-2(1H)-one (A, B) | | 2.19 | 1.61 min (a) | (M + H)$^+$ 501 |
| 3-pyrazol-1-yl-benzylamine | 3a-(3-(trifluoromethyl)-5,6,7,8-tetrahydro-1,6-naphthyridine-6-carbonyl)hexahydro-pentalen-2(1H)-one (A, B) | | 2.20 | 1.79 min (a) | (M + H)$^+$ 510 |
| 3-trifluoromethyl-benzylamine | 3a-(3-(trifluoromethyl)-5,6,7,8-tetrahydro-1,6-naphthyridine-6-carbonyl)hexahydro-pentalen-2(1H)-one (A, B) | | 2.21 | 2.22 min (a) | (M + H)$^+$ 512 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 2-trifluoromethyl-benzylamine | 3a-(3-(trifluoromethyl)-5,6,7,8-tetrahydro-1,6-naphthyridine-6-carbonyl)hexahydro-pentalen-2(1H)-one (A, B) | | 2.22 | 1.95 min (a) | (M + H)$^+$ 512 |
| 2,4-dichloro-benzylamine | 3a-(3-(trifluoromethyl)-5,6,7,8-tetrahydro-1,6-naphthyridine-6-carbonyl)hexahydro-pentalen-2(1H)-one (A, B) | | 2.23 | 1.99 min (a) | (M + H)$^+$ 512 |
| 3,4-dichloro-benzylamine | 3a-(3-(trifluoromethyl)-5,6,7,8-tetrahydro-1,6-naphthyridine-6-carbonyl)hexahydro-pentalen-2(1H)-one (A, B) | | 2.24 | 2.07 min (a) | (M + H)$^+$ 512 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| biphenyl-4-yl-methylamine | 3a-(3-(trifluoromethyl)-5,6,7,8-tetrahydro-1,6-naphthyridine-6-carbonyl)hexahydropentalen-2(1H)-one (A, B) | | 2.25 | 2.08 min (a) | (M + H)$^+$ 520 |
| 2-trifluoromethoxy-benzylamine | 3a-(3-(trifluoromethyl)-5,6,7,8-tetrahydro-1,6-naphthyridine-6-carbonyl)hexahydropentalen-2(1H)-one (A, B) | | 2.26 | 2.08 min (a) | (M + H)$^+$ 528 |
| 3-trifluoromethoxy-benzylamine | 3a-(3-(trifluoromethyl)-5,6,7,8-tetrahydro-1,6-naphthyridine-6-carbonyl)hexahydropentalen-2(1H)-one (A, B) | | 2.27 | 2.06 min (a) | (M + H)$^+$ 528 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| N-(4-aminomethyl-phenyl)-methane sulfonamide | 3a-(3-(trifluoromethyl)-5,6,7,8-tetrahydro-1,6-naphthyridine-6-carbonyl)hexahydro-pentalen-2(1H)-one (A, B) | | 2.28 | 1.77 min (a) | (M + H)$^+$ 537 |
| indan-2-yl-amine | 3a-(3-(trifluoromethyl)-5,6,7,8-tetrahydro-1,6-naphthyridine-6-carbonyl)hexahydro-pentalen-2(1H)-one (A, B) | | 2.29 | 1.86 min (a) | (M + H)$^+$ 470 |
| 2-o-tolyl-ethylamine | 3a-(3-(trifluoromethyl)-5,6,7,8-tetrahydro-1,6-naphthyridine-6-carbonyl)hexahydro-pentalen-2(1H)-one (A, B) | | 2.30 | 1.94 min (a) | (M + H)$^+$ 472 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 2-p-tolyl-ethylamine | 3a-(3-(trifluoromethyl)-5,6,7,8-tetrahydro-1,6-naphthyridine-6-carbonyl)hexahydro-pentalen-2(1H)-one (A, B) | | 2.31 | 1.94 min (a) | (M + H)$^+$ 472 |
| 2-m-tolyl-ethylamine | 3a-(3-(trifluoromethyl)-5,6,7,8-tetrahydro-1,6-naphthyridine-6-carbonyl)hexahydro-pentalen-2(1H)-one (A, B) | | 2.32 | 1.94 min (a) | (M + H)$^+$ 472 |
| 4-(2-amino-ethyl)-phenol | 3a-(3-(trifluoromethyl)-5,6,7,8-tetrahydro-1,6-naphthyridine-6-carbonyl)hexahydro-pentalen-2(1H)-one (A, B) | | 2.33 | 1.69 min (a) | (M + H)$^+$ 474 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 2-(2,5-dimethyl-phenyl)-ethylamine | 3a-(3-(trifluoromethyl)-5,6,7,8-tetrahydro-1,6-naphthyridine-6-carbonyl)hexahydro-pentalen-2(1H)-one (A, B) | | 2.34 | 2.02 min (a) | (M + H)$^+$ 486 |
| 2-(2,4-dimethyl-phenyl)-ethylamine | 3a-(3-(trifluoromethyl)-5,6,7,8-tetrahydro-1,6-naphthyridine-6-carbonyl)hexahydro-pentalen-2(1H)-one (A, B) | | 2.35 | 2.06 min (a) | (M + H)$^+$ 486 |
| 2-(4-trifluoromethyl-phenyl)-ethylamine | 3a-(3-(trifluoromethyl)-5,6,7,8-tetrahydro-1,6-naphthyridine-6-carbonyl)hexahydro-pentalen-2(1H)-one (A, B) | | 2.36 | 2.07 min (a) | (M + H)$^+$ 526 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 2-(3-trifluoromethyl-phenyl)-ethylamine | 3a-(3-(trifluoromethyl)-5,6,7,8-tetrahydro-1,6-naphthyridine-6-carbonyl)hexahydro-pentalen-2(1H)-one (A, B) | | 2.37 | 2.03 min (a) | (M + H)$^+$ 526 |
| 2-(3,4-dichloro-phenyl)-ethylamine | 3a-(3-(trifluoromethyl)-5,6,7,8-tetrahydro-1,6-naphthyridine-6-carbonyl)hexahydro-pentalen-2(1H)-one (A, B) | | 2.38 | 2.05 min (a) | (M + H)$^+$ 526 |
| 2-biphenyl-2-yl-ethylamine | 3a-(3-(trifluoromethyl)-5,6,7,8-tetrahydro-1,6-naphthyridine-6-carbonyl)hexahydro-pentalen-2(1H)-one (A, B) | | 2.39 | 2.17 min (a) | (M + H)$^+$ 534 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 2-biphenyl-4-yl-ethylamine | 3a-(3-(trifluoromethyl)-5,6,7,8-tetrahydro-1,6-naphthyridine-6-carbonyl)hexahydropentalen-2(1H)-one (A, B) | | 2.40 | 2.13 min (a) | (M + H)$^+$ 534 |
| (R)-1-phenyl-1-ethylamine | 3a-(3-(trifluoromethyl)-5,6,7,8-tetrahydro-1,6-naphthyridine-6-carbonyl)hexahydropentalen-2(1H)-one (A, B) | | 2.41 | 1.87 min (a) | (M + H)$^+$ 458 |
| (S)-1-phenyl-1-ethylamine | 3a-(3-(trifluoromethyl)-5,6,7,8-tetrahydro-1,6-naphthyridine-6-carbonyl)hexahydropentalen-2(1H)-one (A, B) | | 2.42 | 1.85 min (a) | (M + H)$^+$ 458 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| pyridin-2-yl-methanamine | 3a-(3-(trifluoromethyl)-5,6,7,8-tetrahydro-1,6-naphthyridine-6-carbonyl)hexahydro-pentalen-2(1H)-one (A, B) | | 2.43 | 1.62 min (c) | (M + H)$^+$ 445 |
| 2-(pyridin-2-yl)ethanamine | 3a-(3-(trifluoromethyl)-5,6,7,8-tetrahydro-1,6-naphthyridine-6-carbonyl)hexahydro-pentalen-2(1H)-one (A, B) | | 2.44 | 1.67 min (c) | (M + H)$^+$ 459 |
| 2-(pyridin-3-yl)ethanamine | 3a-(3-(trifluoromethyl)-5,6,7,8-tetrahydro-1,6-naphthyridine-6-carbonyl)hexahydro-pentalen-2(1H)-one (A, B) | | 2.45 | 1.57 min (c) | (M + H)$^+$ 459 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| (5-methylpyrazin-2-yl)-methanamine | 3a-(3-(trifluoromethyl)-5,6,7,8-tetrahydro-1,6-naphthyridine-6-carbonyl)hexahydropentalen-2(1H)-one (A, B) | | 2.46 | 1.57 min (c) | (M + H)$^+$ 460 |
| 2-(thiophen-2-yl)ethanamine | 3a-(3-(trifluoromethyl)-5,6,7,8-tetrahydro-1,6-naphthyridine-6-carbonyl)hexahydropentalen-2(1H)-one (A, B) | | 2.47 | 1.79 min (c) | (M + H)$^+$ 464 |
| 1,1-dioxidotetrahydrothien-3-yl-amine | 3a-(3-(trifluoromethyl)-5,6,7,8-tetrahydro-1,6-naphthyridine-6-carbonyl)hexahydropentalen-2(1H)-one (A, B) | | 2.48 | 1.60 min (c) | (M + H)$^+$ 472 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| Decahydroiso-quinoline | 3a-(3-(trifluoromethyl)-5,6,7,8-tetrahydro-1,6-naphthyridine-6-carbonyl)hexahydro-pentalen-2(1H)-one (A, B) | 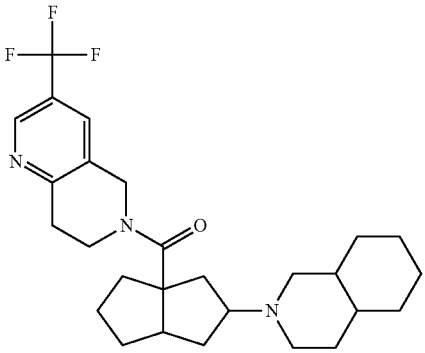 [SMILES: O=C(N1CCc2ncc(C(F)(F)F)cc2C1)C12CCCC1CC(N1CCC3CCCCC3C1)C2] | 2.49 | 1.91 min (c) | (M + H)$^+$ 476 |
| 2-cyclohexyl-pyrrolidine | 3a-(3-(trifluoromethyl)-5,6,7,8-tetrahydro-1,6-naphthyridine-6-carbonyl)hexahydro-pentalen-2(1H)-one (A, B) | 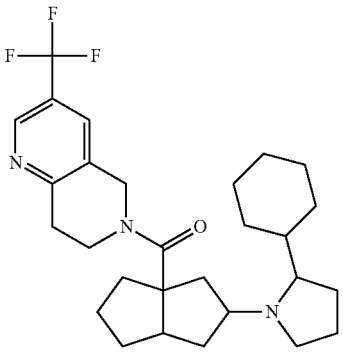 [SMILES: O=C(N1CCc2ncc(C(F)(F)F)cc2C1)C12CCCC1CC(N1CCCC1C1CCCCC1)C2] | 2.50 | 2.02 min (c) | (M + H)$^+$ 490 |
| 4-(pyrrolidin-1-yl)piperidine | 3a-(3-(trifluoromethyl)-5,6,7,8-tetrahydro-1,6-naphthyridine-6-carbonyl)hexahydro-pentalen-2(1H)-one (A, B) | 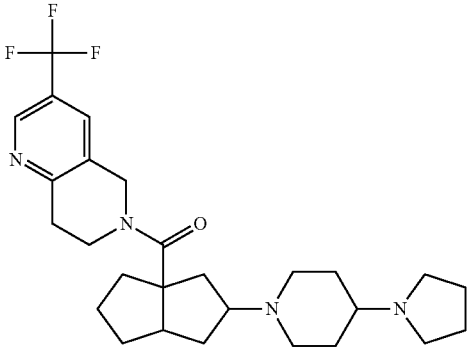 [SMILES: O=C(N1CCc2ncc(C(F)(F)F)cc2C1)C12CCCC1CC(N1CCC(N3CCCC3)CC1)C2] | 2.51 | 1.34 min (c) | (M + H)$^+$ 491 |

TABLE 2-continued

Examples synthesized using general procedure C

| Amine | Core | Product | Ex. # | HPLC R$_t$ (Method) | m/z or $^1$H NMR (d6 DMSO, 400 MHz) |
|---|---|---|---|---|---|
| 2-(1H-indol-3-yl)ethanamine | 3a-(3-(trifluoromethyl)-5,6,7,8-tetrahydro-1,6-naphthyridine-6-carbonyl)hexahydropentalen-2(1H)-one (A, B) | | 2.52 | 1.88 min (c) | (M + H)$^+$ 497 |
| 2-(1-methyl-1H-indol-3-yl)ethanamine | 3a-(3-(trifluoromethyl)-5,6,7,8-tetrahydro-1,6-naphthyridine-6-carbonyl)hexahydropentalen-2(1H)-one (A, B) | | 2.53 | 2.00 min (c) | (M + H)$^+$ 511 |
| piperidin-1-yl(piperidin-2-yl)methanone | 3a-(3-(trifluoromethyl)-5,6,7,8-tetrahydro-1,6-naphthyridine-6-carbonyl)hexahydropentalen-2(1H)-one (A, B) | | 2.54 | 1.76 min (c) | (M + H)$^+$ 533 |

What is claimed is:

1. A compound of Formula (I)

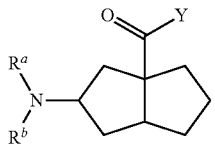

Formula (I)

pharmaceutically acceptable salts, isomers thereof or stereoisomers thereof wherein $R^a$ is H or optionally substituted $(C_1-C_6)$alkyl;

$R^b$ is selected from the optionally substituted group consisting of —$(CH_2)_n$-aryl, —$CH(CH_3)$-aryl, —$(CH_2)_n$-aryl-aryl, —$(CH_2)_n$-aryl-heteroaryl, —$(CH_2)_n$—$(C_3$-$C_8)$cycloalkyl, —$(CH_2)_n$-heterocyclyl and —$(C_3-C_8)$cycloalkyl-aryl; or $R^a$ and $R^b$ are taken together with the nitrogen to form 2,3-dihydro-1H-isoindolyl, decahydroisoquinolinyl, optionally substituted piperidinyl or optionally substituted pyrrolidinyl;

Y is selected from the optionally substituted group consisting of 5,6,7,8-tetrahydro[1,6]naphthridinyl, —NH—$(CH_2)_n$-heterocyclyl wherein the NH is attached to the carbonyl and -heterocyclyl-aryl wherein the heterocyclyl is attached to the carbonyl; and n is 0, 1 or 2.

2. The compound or salt according to claim 1 wherein Y is selected from the optionally substituted group consisting of 5,6,7,8-tetrahydro[1,6]naphthridinyl, —NH—$(CH_2)_2$-pyrrolidinyl and -piperazinyl-phenyl.

3. The compound or salt according to claim 2 wherein $R^a$ is H or methyl.

4. The compound or salt according to claim 3 wherein $R^b$ is selected from the optionally substituted group consisting of —$CH_2$-phenyl, —$CH_2$-phenyl-phenyl, —$(CH_2)_2$-phenyl, —$CH(CH_3)$-phenyl, —$CH_2CH_2$-phenyl-phenyl, —$CH_2$-phenyl-pyrazolyl, phenyl-pyrazolyl, indanyl, —$(CH_2)_2$-indolyl, 1,2,3,4-tetrahydronaphthyl, —$(CH_2)$-pyrazinyl, —$(CH_2)$-pyridinyl, —$(CH_2)_2$-pyridinyl, —$(CH_2)_2$-pyrrolidinyl, —$(CH_2)_2$-thienyl, tetrahydrothienyl-1,1-dioxide, —$(CH_2)_2$-piperidinyl, tetrahydropyranyl and -cyclohexyl-phenyl.

5. The compound or salt according to claim 4 wherein $R^b$ is selected from the optionally substituted group consisting of —$CH_2$-phenyl, —$(CH_2)_2$-phenyl, —$CH_2$-phenyl-pyrazolyl, indanyl, —$(CH_2)$-indolyl, 1,2,3,4-tetrahydronaphthyl, —$(CH_2)_2$-pyridinyl and -cyclohexyl-phenyl.

6. The compound or salt according to claim 5 wherein Y is selected from the optionally substituted group consisting of 5,6,7,8-tetrahydro[1,6]naphthyridinyl and -piperazinyl-phenyl.

7. The compound or salt according to claim 6 wherein $R^b$ is selected from the optionally substituted group consisting of —$CH_2$-phenyl, —$(CH_2)_2$-phenyl, 1,2,3,4-tetrahydronaphthyl, —$CH_2$-phenyl-pyrazolyl, indanyl, —$(CH_2)_2$-pyridinyl and -cyclohexyl-phenyl.

8. The compound or salt according to claim 7 wherein $R^b$ is selected from the optionally substituted group consisting of —$CH_2$-phenyl, 1,2,3,4 tetrahydronaphthyl and -cyclohexyl-phenyl.

9. The compound or salt according to claim 8 wherein $R^b$ is optionally substituted with one or more substituents selected from the group consisting of alkyl, alkoxy, halogen, CN, OH, $CF_3$, $OCF_3$, $NH_2$, $NH(CH_3)$ and $N(CH_3)_2$.

10. The compound or salt according to claim 9 wherein Y is optionally substituted with $CF_3$.

11. The compound or salt according to claim 2 wherein $R^a$ and $R^b$ are taken together with the nitrogen to form 2,3-dihydro-1H-isoindolyl, optionally substituted piperidinyl or optionally substituted pyrrolidinyl.

12. The compound or salt according to claim 11 wherein the optionally substituted piperidinyl or optionally substituted pyrrolidinyl is optionally substituted by substituents selected from the group consisting of optionally substituted cyclohexyl and optionally substituted phenyl.

13. The compound or salt according to claim 12 wherein Y is optionally substituted 5,6,7,8-tetrahydro[1,6]naphthyridinyl.

14. The compound or salt according to claim 13 wherein the optionally substituted piperidinyl is substituted with optionally substituted phenyl or optionally substituted pyrrolidinyl.

15. The compound or salt according to claim 14 wherein the optionally substituted piperidinyl is substituted with optionally substituted pyrrolidinyl.

16. The compound or salt according to claim 14 wherein the optionally substituted piperidinyl is substituted with optionally substituted phenyl.

17. The compound or salt according to claim 12 wherein the optionally substituted pyrrolidinyl is substituted by optionally substituted cyclohexyl.

18. A pharmaceutical composition comprising a compound of Formula (I)

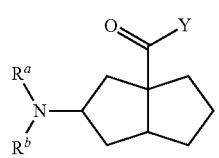

Formula (I)

or a pharmaceutically acceptable salt thereof, and a pharmaceutically acceptable carrier or excipient, wherein $R^a$ is H or optionally substituted $(C_1-C_6)$alkyl;

$R^b$ is selected from the optionally substituted group consisting of —$(CH_2)_n$-aryl, —$CH(CH_3)$-aryl, —$(CH_2)_n$-aryl-aryl, —$(CH_2)_n$-aryl-heteroaryl, —$(CH_2)_n$—$(C_3$-$C_8)$cycloalkyl, —$(CH_2)_n$-heterocyclyl and —$(C_3-C_8)$cycloalkyl-aryl; or $R^a$ and $R^b$ are taken together with the nitrogen to form 2,3-dihydro-1H-isoindolyl, decahydroisoquinolinyl, optionally substituted piperidinyl or optionally substituted pyrrolidinyl;

Y is selected from the optionally substituted group consisting of 5,6,7,8-tetrahydro[1,6]naphthyridinyl, —NH—$(CH_2)_n$-heterocyclyl wherein the NH is attached to the carbonyl and -heterocyclyl-aryl wherein the heterocyclyl is attached to the carbonyl; and n is 0, 1 or 2.

19. The compound or salt according to claim 1, wherein the compound is selected from the group consisting of:

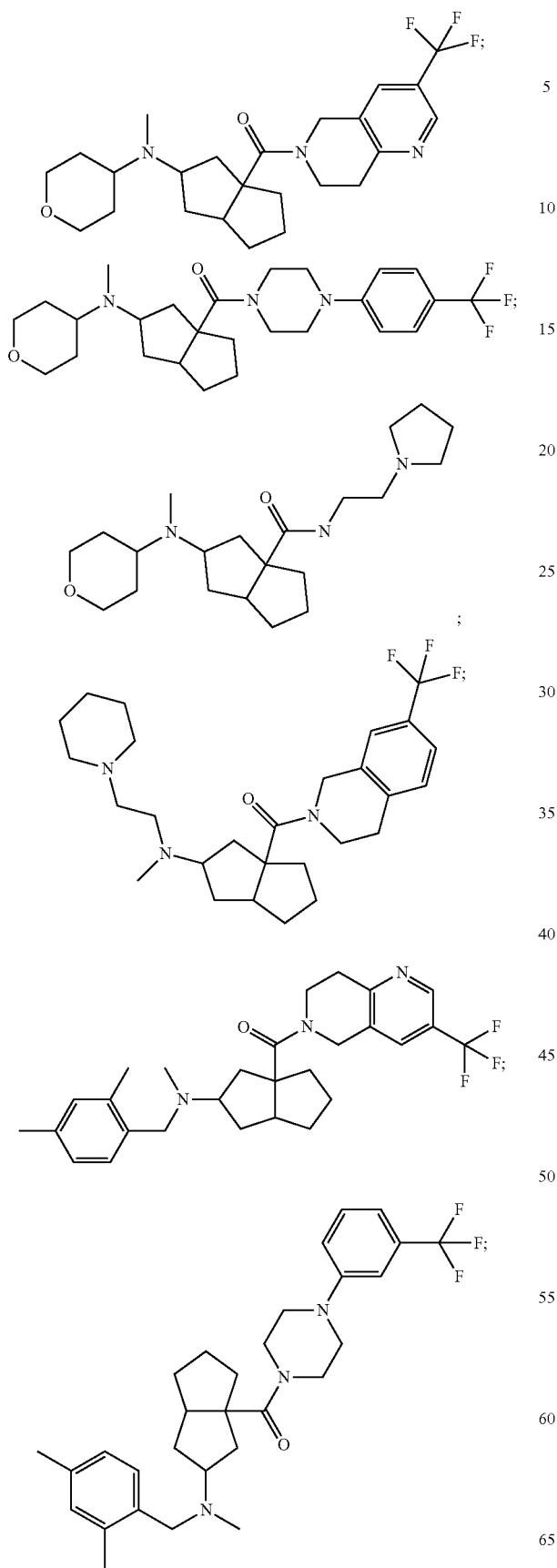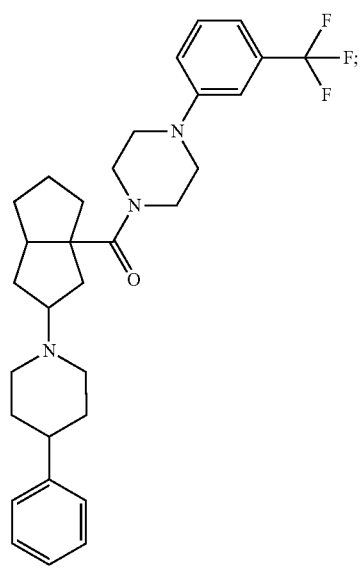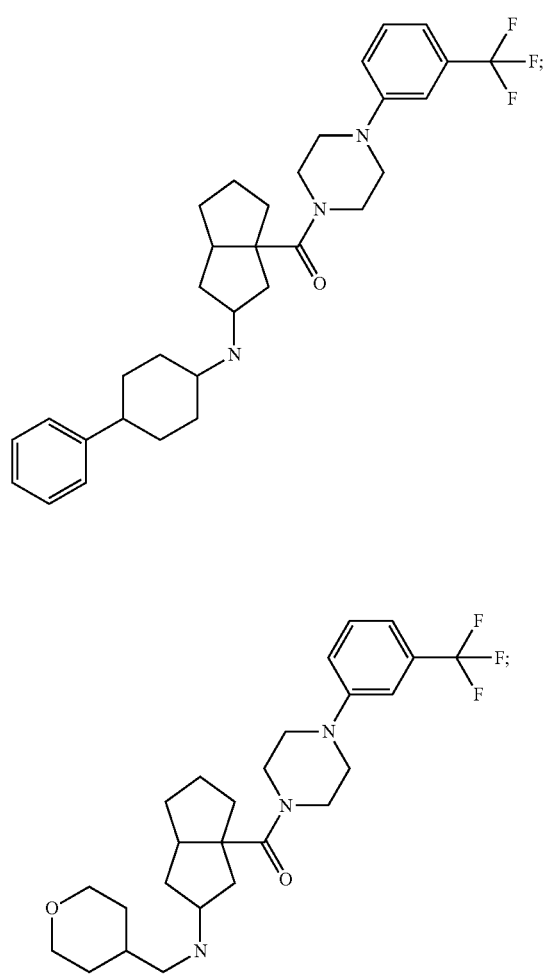

81
-continued
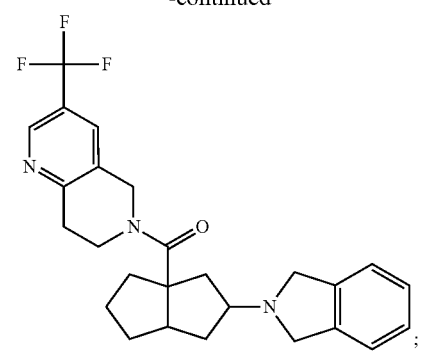
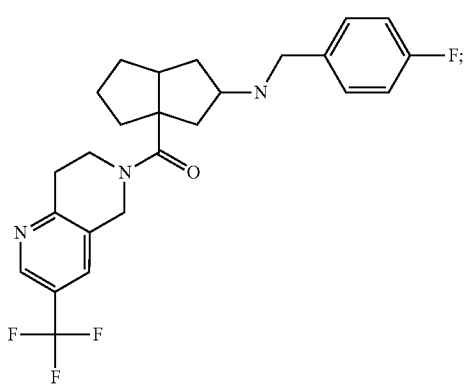
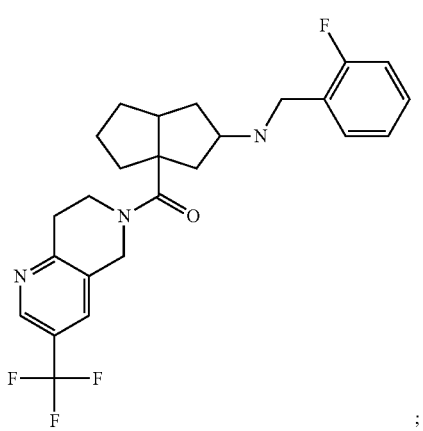
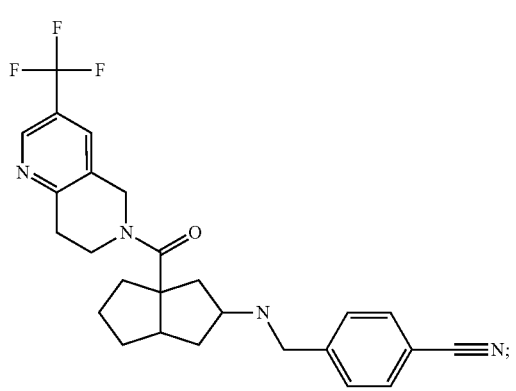
82
-continued
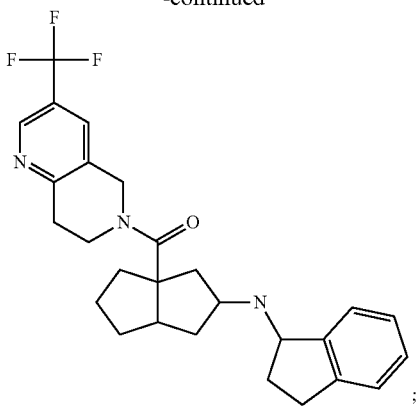
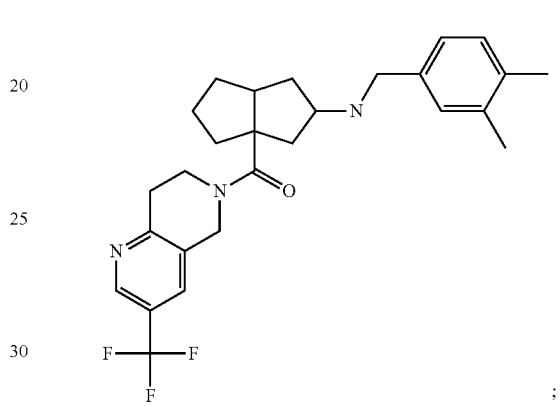
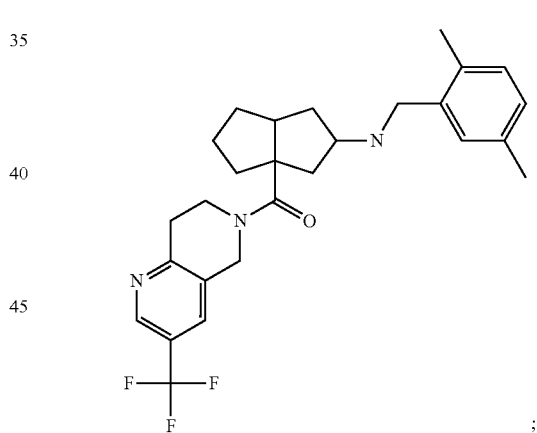
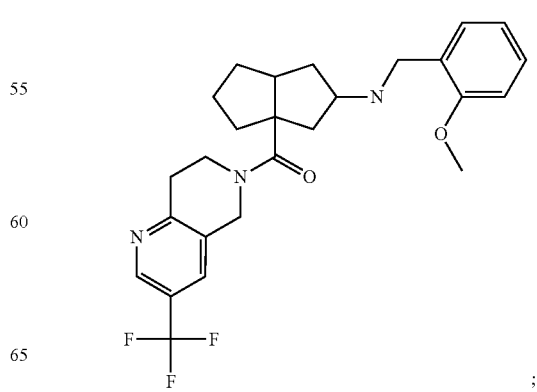

83
-continued
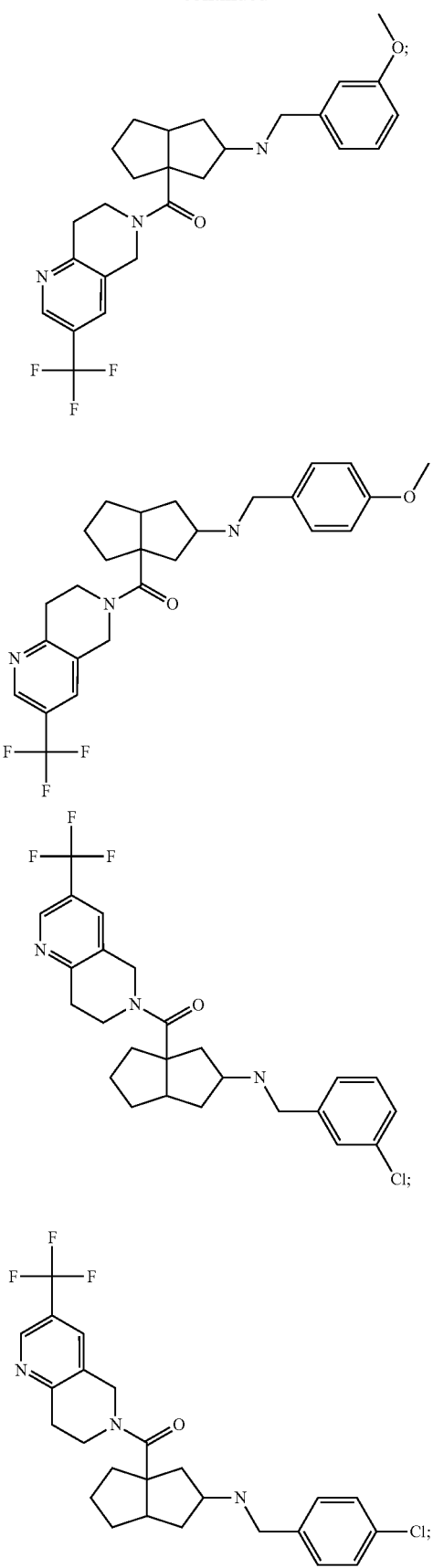
84
-continued
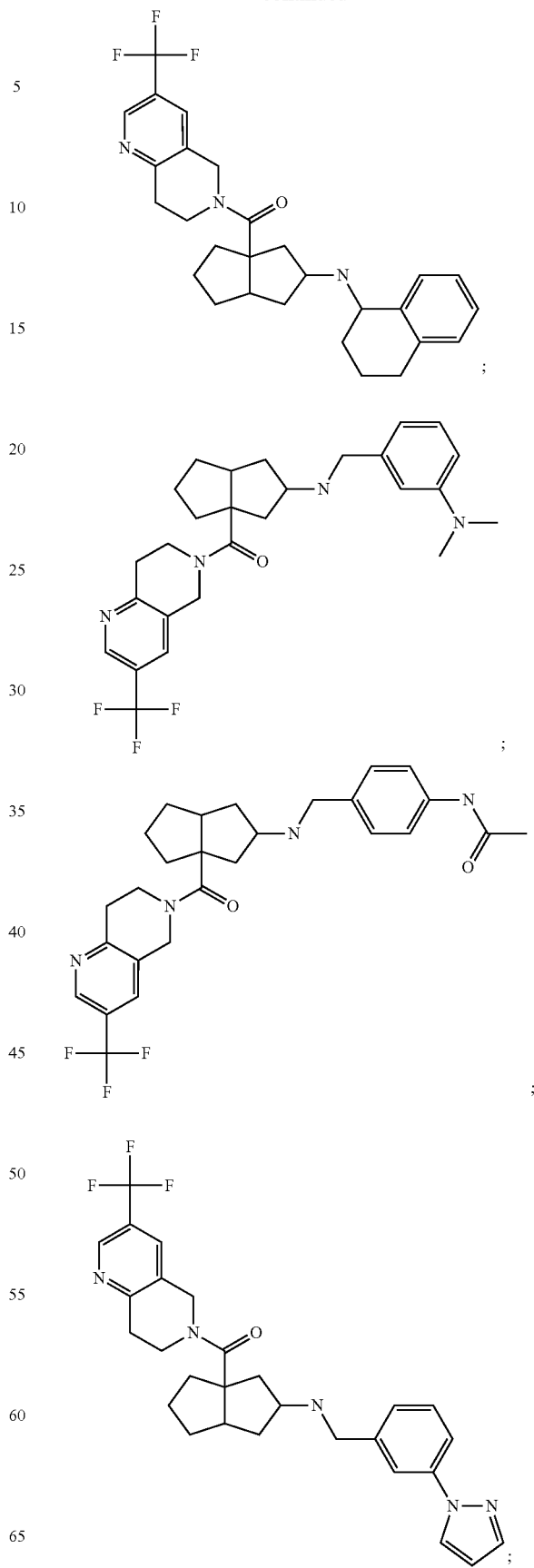

85
-continued
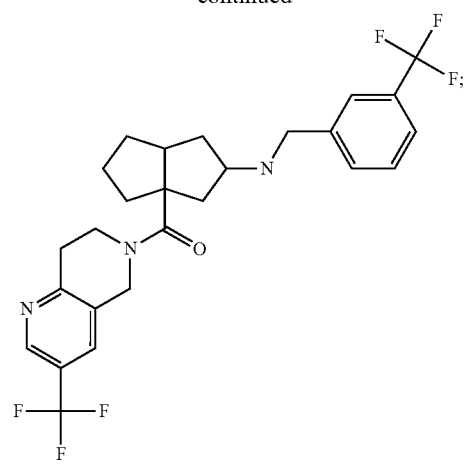
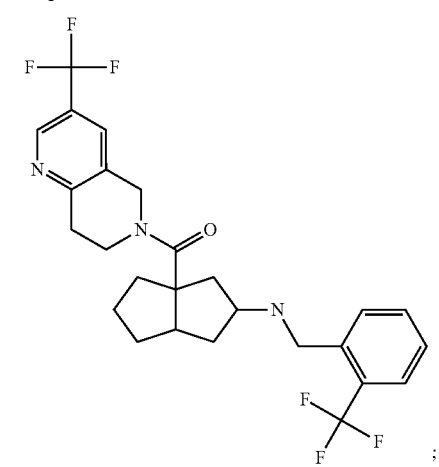
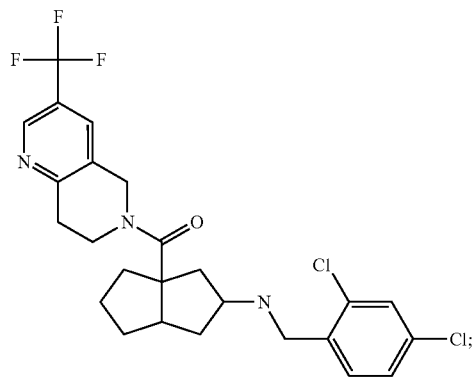
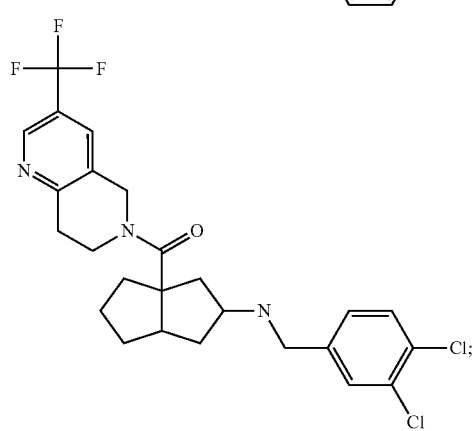
86
-continued
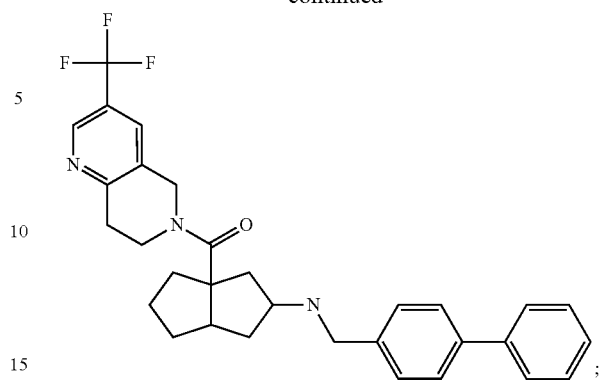
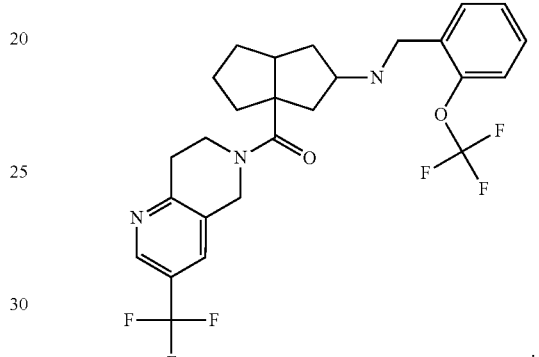
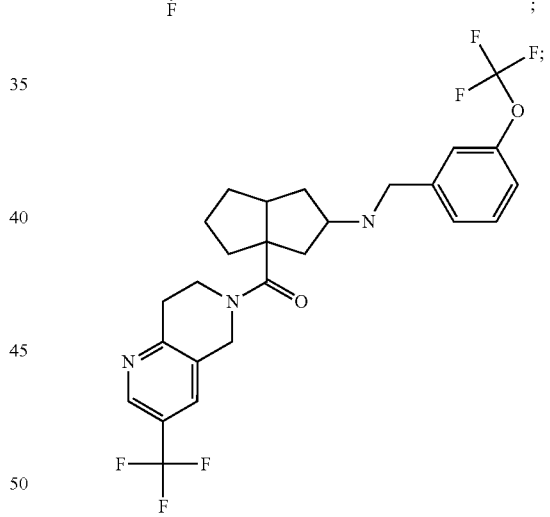
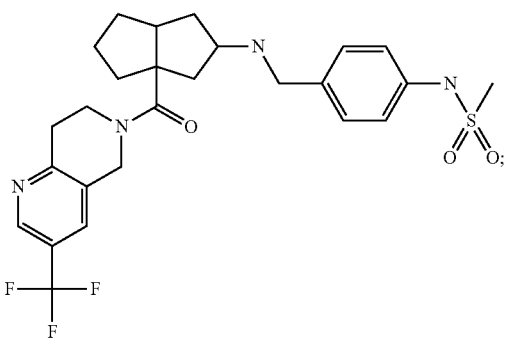

87
-continued
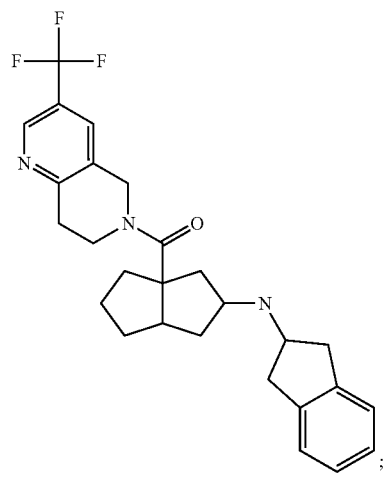
88
-continued
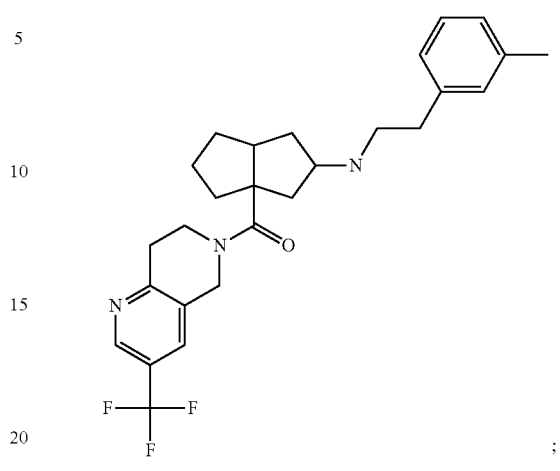
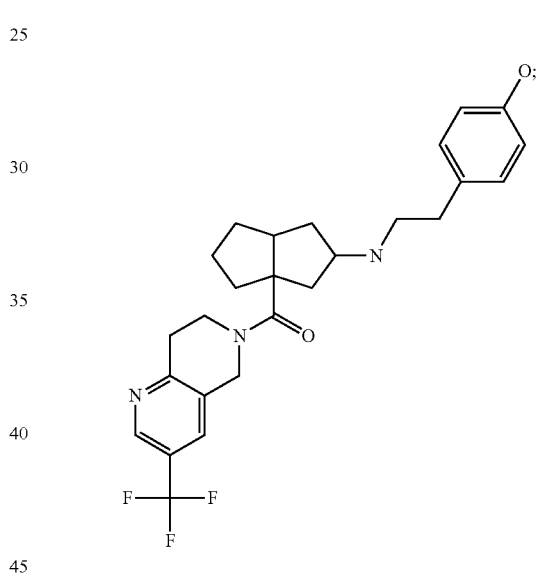
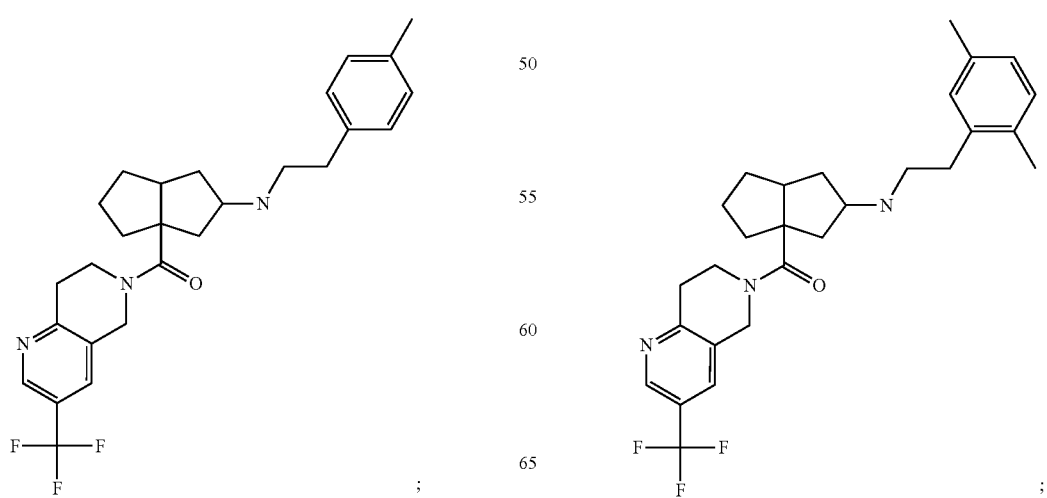

89
-continued
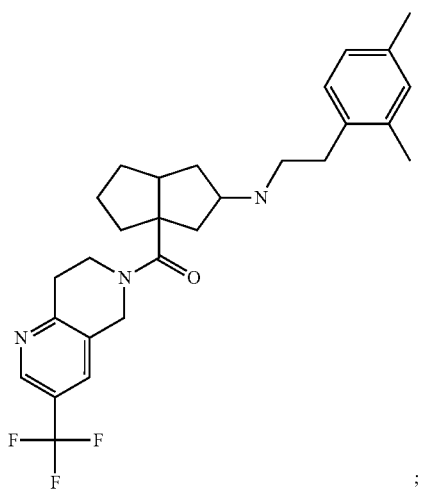
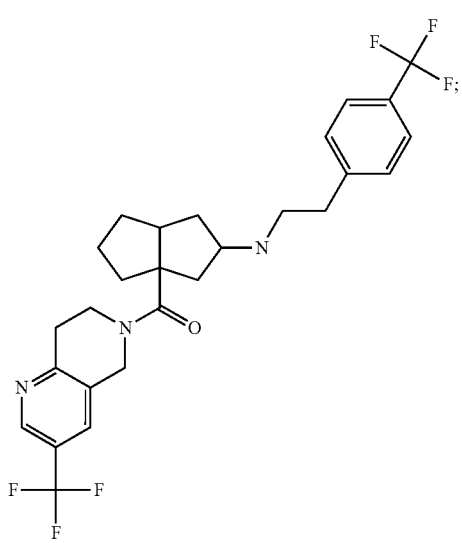
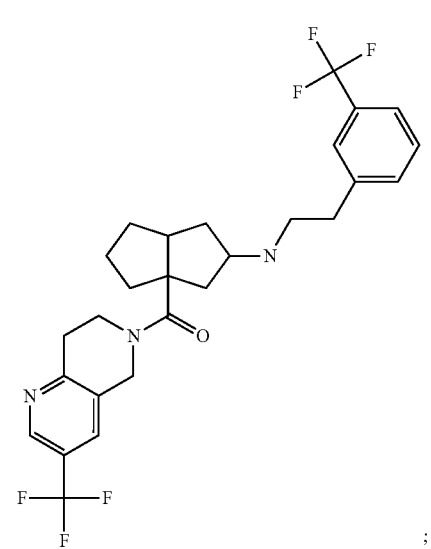
90
-continued
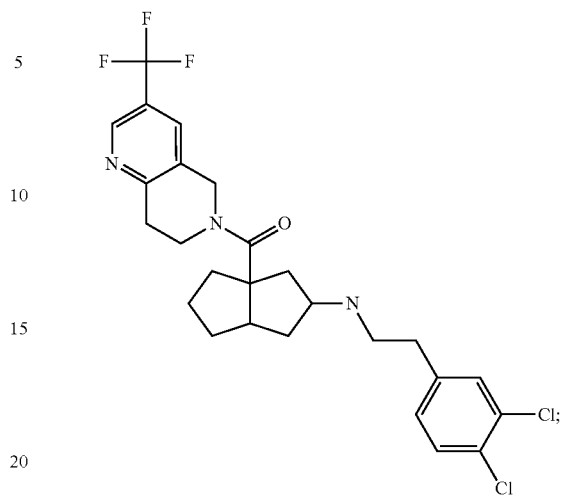
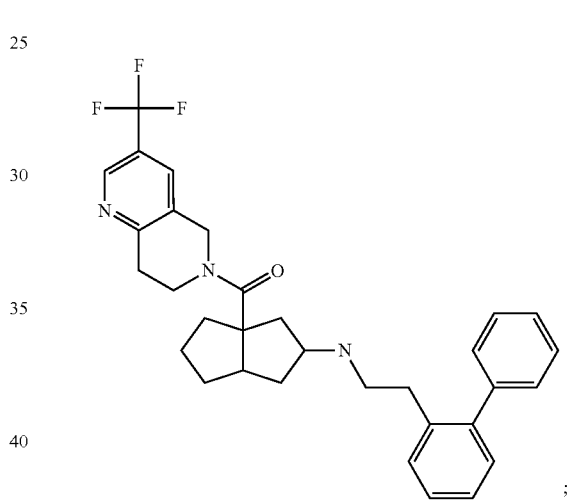
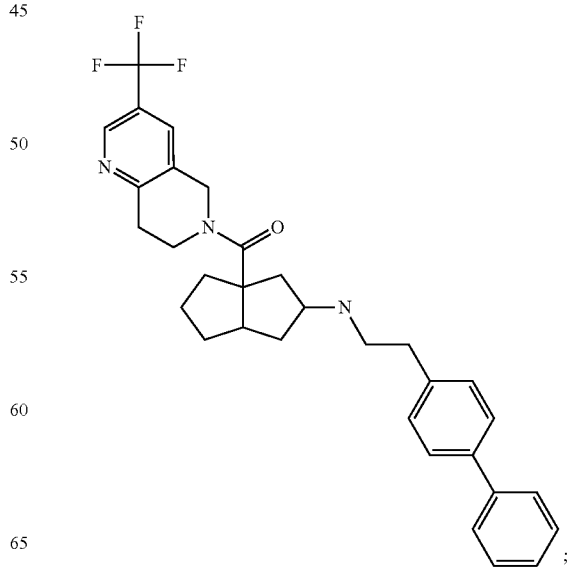

91
-continued
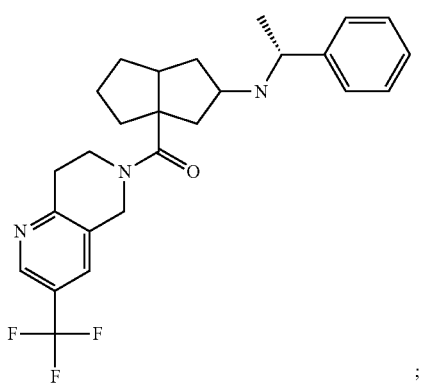
;
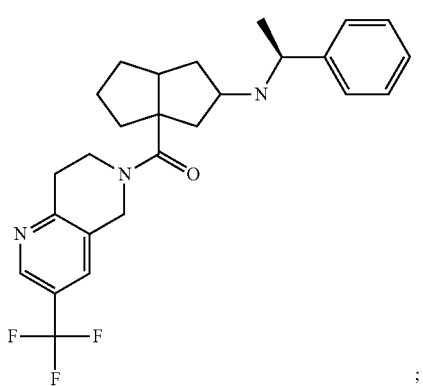
;
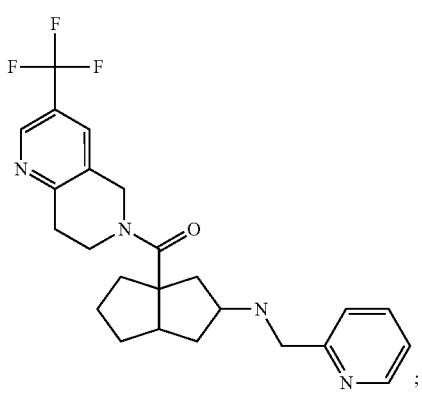
;
92
-continued
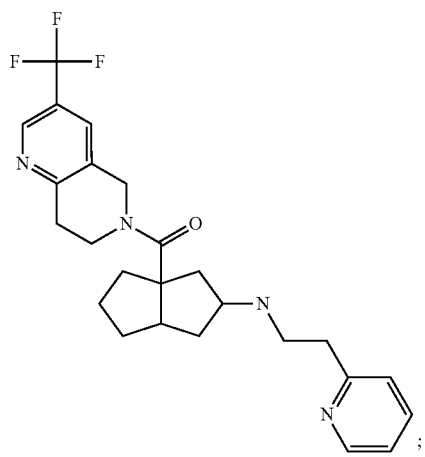
;
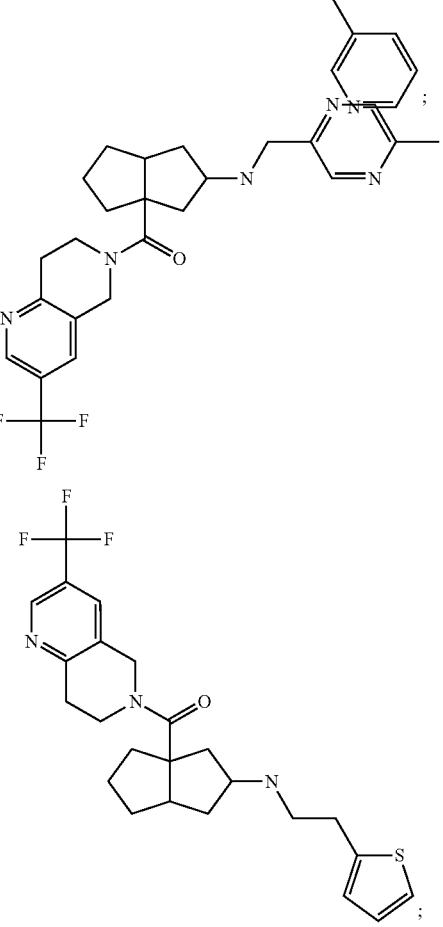

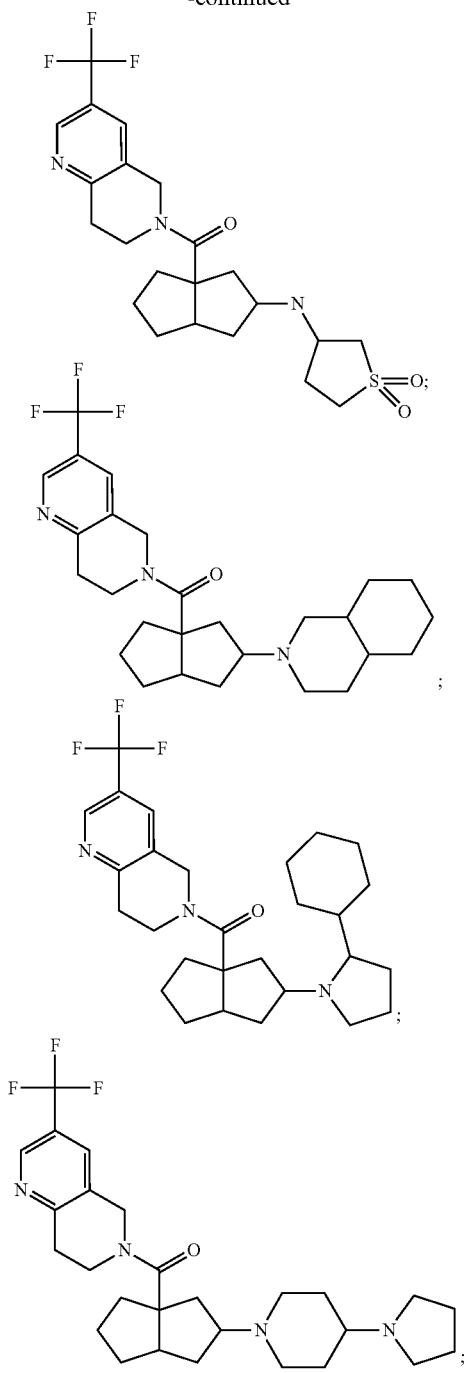
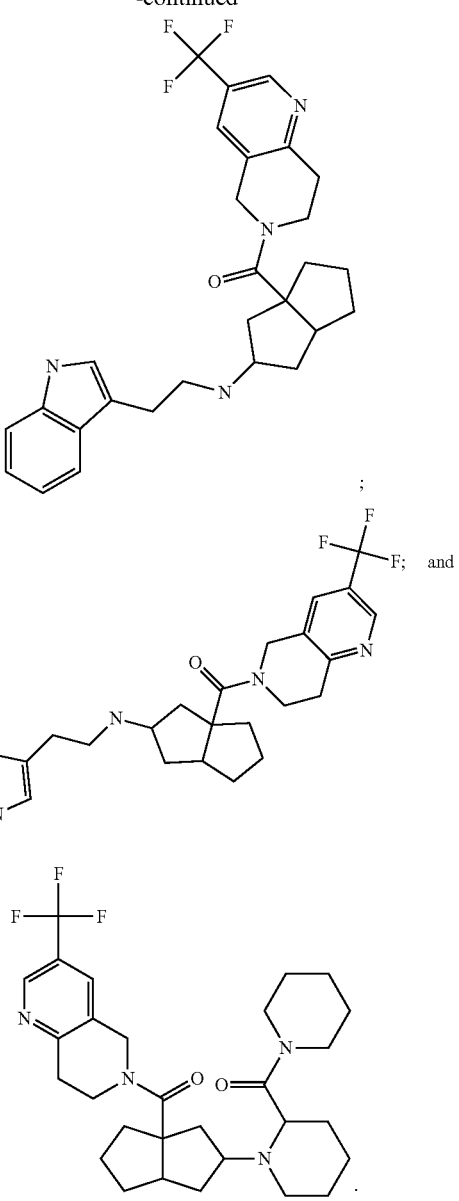
20. A pharmaceutical composition comprising a compound of claim 19, or a pharmaceutically acceptable salt thereof, and a pharmaceutically acceptable carrier or excipient.
* * * * *